United States Patent
Pignede et al.

(10) Patent No.: US 11,473,072 B2
(45) Date of Patent: Oct. 18, 2022

(54) ***SACCHAROMYCES CEREVISIAE* STRAINS EXPRESSING EXOGENOUS GLUCOAMYLASE AND XYLANASE ENZYMES AND THEIR USE IN THE PRODUCTION OF BIOETHANOL**

(71) Applicant: LESAFFRE ET COMPAGNIE, Paris (FR)

(72) Inventors: Georges Pignede, Marc en Baroeul (FR); Maud Petit, Quesnoy sur Deule (FR); Benoît Thomas, Marc en Baroeul (FR); Sébastien Hulin, Lille (FR)

(73) Assignee: LESAFFRE ET COMPAGNIE, Paris (FR)

( * ) Notice: Subject to any disclaimer, the term of this patent is extended or adjusted under 35 U.S.C. 154(b) by 0 days.

(21) Appl. No.: 17/257,107

(22) PCT Filed: Jul. 2, 2019

(86) PCT No.: PCT/EP2019/067668
§ 371 (c)(1),
(2) Date: Dec. 30, 2020

(87) PCT Pub. No.: WO2020/007823
PCT Pub. Date: Jan. 9, 2020

(65) Prior Publication Data
US 2021/0261934 A1 Aug. 26, 2021

(30) Foreign Application Priority Data
Jul. 2, 2018 (FR) ...................................... 18 56080

(51) Int. Cl.
*C12N 9/24* (2006.01)
*C12P 7/06* (2006.01)

(52) U.S. Cl.
CPC .............. *C12N 9/2402* (2013.01); *C12P 7/06* (2013.01); *C12Y 302/01003* (2013.01); *C12Y 302/01008* (2013.01)

(58) Field of Classification Search
CPC .... C12Y 302/01003; C12Y 302/01008; C12N 9/2402; C12N 15/81; C12N 1/18; Y02E 50/10; C07K 14/395; C12P 7/06
See application file for complete search history.

(56) References Cited

U.S. PATENT DOCUMENTS

| | | | | |
|---|---|---|---|---|
| 7,314,743 B2 * | 1/2008 | Clarkson | .............. | C12N 9/2434 435/200 |
| 9,206,444 B2 * | 12/2015 | Brevnova | .............. | C12N 15/52 |
| 10,947,519 B2 * | 3/2021 | Petit | .......................... | C12P 7/06 |

FOREIGN PATENT DOCUMENTS

| | | | | |
|---|---|---|---|---|
| FR | WO/2017/037362_MT | * | 3/2017 | ............. C12N 15/81 |
| WO | 2009/137574 A2 | | 11/2009 | |
| WO | 2017/037362 A1 | | 3/2017 | |

OTHER PUBLICATIONS

Sadowski et al., The sequence-structure relationship and protein function prediction. Current Opinion in Structural Biology, 2009, vol. 19: 357-362. (Year: 2009).*
Seffernick et al., Melamine deaminase and Atrazine chlorohydrolase: 98 percent identical but functionally different. J. Bacteriol., 2001, vol. 183 (8): 2405-2410. 2001 (Year: 2001).*
Tang et al., Identification of Dehalobacter reductive dehydrogenases that catalyse dechlorination of chloroform, 1,1,1-trichloroethane and 1,1-dichloroethane. Phil Trans R Soc B, 2013, vol. 368: Mar. 18, 2012, pp. 1-10. (Year: 2013).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
International Search Report (with English translation) dated Sep. 25, 2019 in International Application No. PCT/EP2019/067668; 9 pages.
Written Opinion dated Sep. 25, 2019 in International Application No. PCT/EP2019/067668; 6 pages.
Andriy Y. Voronovsky et al., "Development of strains of the thermotolerant yeast Hansenula polymorpha capable of alcoholic fermentation of starch and xylan", Metabolic Engineering, Academic Press, US. vol. 11, No. 4-5, Jul. 1, 2009, pp. 234-242.

* cited by examiner

*Primary Examiner* — Ganapathirama Raghu
(74) *Attorney, Agent, or Firm* — Maier & Maier, PLLC

(57) ABSTRACT

Strains of *Saccharomyces cerevisiae* yeast that are genetically modified so as to co-express a gene coding a glucoamylase of fungal origin, a gene coding a glucoamylase of *Saccharomyces cerevisiae* var. *diastaticus*, and a gene coding a xylanase of fungal origin. The production yield of bioethanol through these strains is greater than that of strains that are otherwise identical but that do not include the gene coding the xylanase of fungal origin. Also, a method for obtaining these yeasts, as well as the use of these yeasts in the production of bioethanol.

10 Claims, 3 Drawing Sheets

Specification includes a Sequence Listing.

SACCHAROMYCES CEREVISIAE STRAINS EXPRESSING EXOGENOUS GLUCOAMYLASE AND XYLANASE ENZYMES AND THEIR USE IN THE PRODUCTION OF BIOETHANOL

CROSS-REFERENCE TO RELATED APPLICATIONS

The present patent application is filed pursuant to 35 U.S.C. § 371 as a U.S. National Phase application of International Patent Application No. PCT/FR2019/067668, filed on Jul. 2, 2019, claiming the benefit of priority to French Patent Application No. FR 18 56080, filed on Jul. 2, 2018. The content of each of the aforementioned patent applications is incorporated herein by reference in its entirety.

FIELD

The present invention relates to *Saccharomyces cerevisiae* yeast strains genetically modified so as to co-express genes encoding glucoamylases of fungal origin and *Saccharomyces cerevisiae* var. *diastaticus*, and a gene encoding a xylanase of fungal origin. Such strains find particular application in the production of biofuel, in particular bioethanol. The present invention also relates to a process for obtaining these yeasts as well as the use of these yeasts in the production of bioethanol.

BACKGROUND

The decrease in non-renewable energy resources and the rising concern about the increase in greenhouse gas emissions are source of the need to find alternative energy sources to fossil fuels (oil, coal, gas). Plant biomass from forests, agricultural or agri-food products and/or co-products constitutes a considerable source of carbon for the production of molecules of industrial interest. Ethanol produced from the fermentable sugars contained in plants is used in vehicles equipped with combustion engines. Bioethanol production has thus developed rapidly in recent years, with world bioethanol production more than doubling in less than ten years (49.5 billion liters produced in 2007 versus 102 billion liters in 2016—www.ethanolrfa.org/resources/industry/statistics/, Renewable Fuels Association). The United States and Brazil remain the two largest bioethanol producing countries, with their combined production representing 85% of global production.

So-called first-generation bioethanol is produced by fermentation of the hexoses (six-carbon sugars) contained in biomasses rich in starch (grains of corn, barley, wheat, cassava, potato tubers, etc.) or in sucrose (sugar cane, sugar beet, sugar sorghum, etc.), while so-called second-generation bioethanol is generated by transformation of the cellulose and hemicellulose contained in agricultural residues such as cereal straw, corn cane, forest residues, wood, energy crops such as switchgrass or short or very short rotation coppices (poplar for example).

Only first-generation bioethanol is prepared on an industrial scale today. Industrial preparation comprises the use of *Saccharomyces cerevisiae* yeast strains, which ferment the glucose from biomass to ethanol with high alcoholic strength, productivity and yield. The process for converting starch to bioethanol involves pre-hydrolysis and liquefaction of the biomass starch, conversion of the liquefied starch to fermentable sugars (by starch hydrolysis), and fermentation of these sugars to ethanol—the latter two steps often being carried out simultaneously. Starch hydrolysis requires the action of so-called amylolytic enzymes. Since *Saccharomyces cerevisiae* yeasts are generally devoid of such enzymes, the production of ethanol from biomass composed of starch is carried out in two steps: a first step of adding amylolytic enzymes to the biomass in order to pre-hydrolyze and liquefy the starch contained in the biomass, and a second step where other enzymes (amylolytic enzymes, enzyme cocktails, proteases, and/or trehalase, etc.) are used to hydrolyze the liquefied starch and a *Saccharomyces cerevisiae* strain to ferment the fermentable sugars thus released.

With the aim to simplify the production of bioethanol from biomass composed of starch, the present Applicant has developed *Saccharomyces cerevisiae* strains comprising, integrated into their genome, exogenous glucoamylase genes. These genetically modified *Saccharomyces cerevisiae* strains allow the simultaneous partial hydrolysis of liquefied starch and alcoholic fermentation (WO 2017/037362). Despite the increased performance of the *Saccharomyces cerevisiae* strains thus modified, there remains a need for new and improved yeast strains for the production of first-generation ethanol.

SUMMARY

Generally, the present invention relates to *Saccharomyces cerevisiae* yeast strains which have improved properties compared with specialized yeast strains commonly used in the production of first-generation bioethanol, and also compared with *Saccharomyces cerevisiae* strains comprising, integrated in their genome, exogenous glucoamylase genes (WO 2017/037362). More specifically, the Inventors of the present invention have developed a genetically modified *Saccharomyces cerevisiae* strain, said strain co-expressing several heterologous glucoamylase genes, and a heterologous xylanase gene. In particular, the *Saccharomyces cerevisiae* strains according to the invention co-express both a gene encoding a glucoamylase of fungal origin and a gene encoding glucoamylase from *Saccharomyces cerevisiae* var. *diastaticus*, as well as a xylanase gene of fungal origin. The Inventors demonstrated that these strains were capable of hydrolyzing the liquefied starch extracted from the biomass while efficiently fermenting the sugars derived from this hydrolysis. Indeed, the use of a yeast strain according to the present invention makes it possible to replace all or part of the amount of exogenous enzymes required during the conversion of the liquefied starch into bioethanol and produces bioethanol with a higher yield than the strains known in the art.

Thus, according to a first aspect, the present invention relates to a *Saccharomyces cerevisiae* yeast strain, characterized in that it co-expresses:
 a gene encoding a xylanase of fungal origin;
 a gene encoding a glucoamylase of fungal origin; and
 a gene encoding glucoamylase from *Saccharomyces cerevisiae* var. *diastaticus*.

In certain embodiments, the xylanase of fungal origin is an *Aspergillus niger* xylanase or a *Trichoderma reesei* xylanase. In particular, the xylanase of fungal origin may be an *Aspergillus niger* xylanase which is encoded by the nucleic sequence SEQ ID NO: 5 or which consists of the polypeptide sequence SEQ ID NO: 6 or a functional variant of the polypeptide sequence SEQ ID NO: 6. Alternatively, the xylanase of fungal origin may be a *Trichoderma reesei* xylanase which is encoded by the nucleic sequence SEQ ID NO: 7 or which consists of the polypeptide sequence SEQ ID NO: 8 or a functional variant of the polypeptide sequence SEQ ID NO: 8.

In certain embodiments, the glucoamylase from *Saccharomyces cerevisiae* var. *diastaticus* is encoded by the nucleic sequence SEQ ID NO: 3 or consists of the polypeptide sequence SEQ ID NO: 4 or a functional variant of the polypeptide sequence SEQ ID NO: 4.

In certain embodiments, the glucoamylase of fungal origin is selected from the group consisting of: *Aspergillus niger* glucoamylase, *Saccharomycopsis fibuligera* glucoamylase, *Trichoderma reesei* glucoamylase, *Thermomyces lanuginosus* glucoamylase, *Rhizopus oryzae* glucoamylase and *Aspergillus oryzae* glucoamylase. In particular, the glucoamylase of fungal origin may be an *Aspergillus niger* glucoamylase which is encoded by the nucleic sequence SEQ ID NO: 1 or which consists of the polypeptide sequence SEQ ID NO: 2 or a functional variant of the polypeptide sequence SEQ ID NO: 2.

In certain embodiments, the *Saccharomyces cerevisiae* yeast strain according to the invention comprises:
  m copies of the gene encoding xylanase of fungal origin;
  n copies of the gene encoding glucoamylase of fungal origin; and
  p copies of the gene encoding glucoamylase from *Saccharomyces cerevisiae* var. *diastaticus*,
where m is an integer comprised between 1 and 10, n is an integer comprised between 2 and 10, and p is an integer comprised between 2 and 10.

In certain embodiments, m is 1 or 4.

In some embodiments, n is 6 and p is 4.

In certain embodiments, the gene encoding xylanase of fungal origin, the gene encoding glucoamylase of fungal origin, and the gene encoding glucoamylase from *Saccharomyces cerevisiae* var. *diastaticus* are integrated into the genome of the *Saccharomyces cerevisiae* yeast strain according to the invention.

In certain embodiments, the *Saccharomyces cerevisiae* yeast strain according to the invention is the strain deposited on 26 Apr. 2017 in the CNCM under number I-5201.

In another aspect, the present invention relates to a method for obtaining a *Saccharomyces cerevisiae* yeast strain useful for the production of bioethanol, said method comprising the steps consisting in:
(a) genetically modifying a *Saccharomyces cerevisiae* yeast so that it co-expresses a gene encoding a xylanase of fungal origin, a gene encoding a glucoamylase of fungal origin, and a gene encoding glucoamylase from *Saccharomyces cerevisiae* var. *diastaticus* or obtaining a *Saccharomyces cerevisiae* yeast strain as described herein;
(b) culturing and fermenting the yeast obtained in step (a) on a synthetic dextrin medium; and
(c) selecting at least one strain with fermentation kinetics at least equal to or greater than the fermentation kinetics of the strain deposited on 9 Jul. 2015 in the CNCM under number I-4997.

In another aspect, the present invention relates to a method for increasing the bioethanol production yield of a *Saccharomyces cerevisiae* yeast strain, said method comprising the steps consisting in:
(a) providing a *Saccharomyces cerevisiae* yeast co-expressing a gene encoding a glucoamylase of fungal origin, and a gene encoding glucoamylase from *Saccharomyces cerevisiae* var. *diastaticus*;
(b) genetically modifying the yeast of step (a) so that it further expresses a gene encoding a xylanase of fungal origin;
(c) culturing and fermenting the yeast obtained in step (b) on a synthetic dextrin medium; and
(d) selecting at least one strain with fermentation kinetics at least equal to or greater than the fermentation kinetics of the strain deposited on 9 Jul. 2015 in the CNCM under number I-4997.

In certain embodiments, the method for increasing the bioethanol production yield of a *Saccharomyces cerevisiae* yeast strain is characterized in that the *Saccharomyces cerevisiae* yeast of step (a) is the *Saccharomyces cerevisiae* yeast strain deposited on 9 Jul. 2015 in the CNCM under number I-4997.

In another aspect, the present invention relates to a method for producing bioethanol from a biomass, said biomass method comprising the steps consisting in:
(a) pre-hydrolyzing and liquefying the starch from the biomass;
(b) reacting the liquefied starch obtained in step (a) with a *Saccharomyces cerevisiae* yeast strain according to the invention to produce bioethanol; and
(c) extracting the bioethanol produced in step (b).

Finally, the present invention also relates to the use of a *Saccharomyces cerevisiae* yeast strain disclosed herein, for the production of bioethanol.

A more detailed description of certain preferred embodiments of the invention is given below.

DETAILED DESCRIPTION

Figure 1:
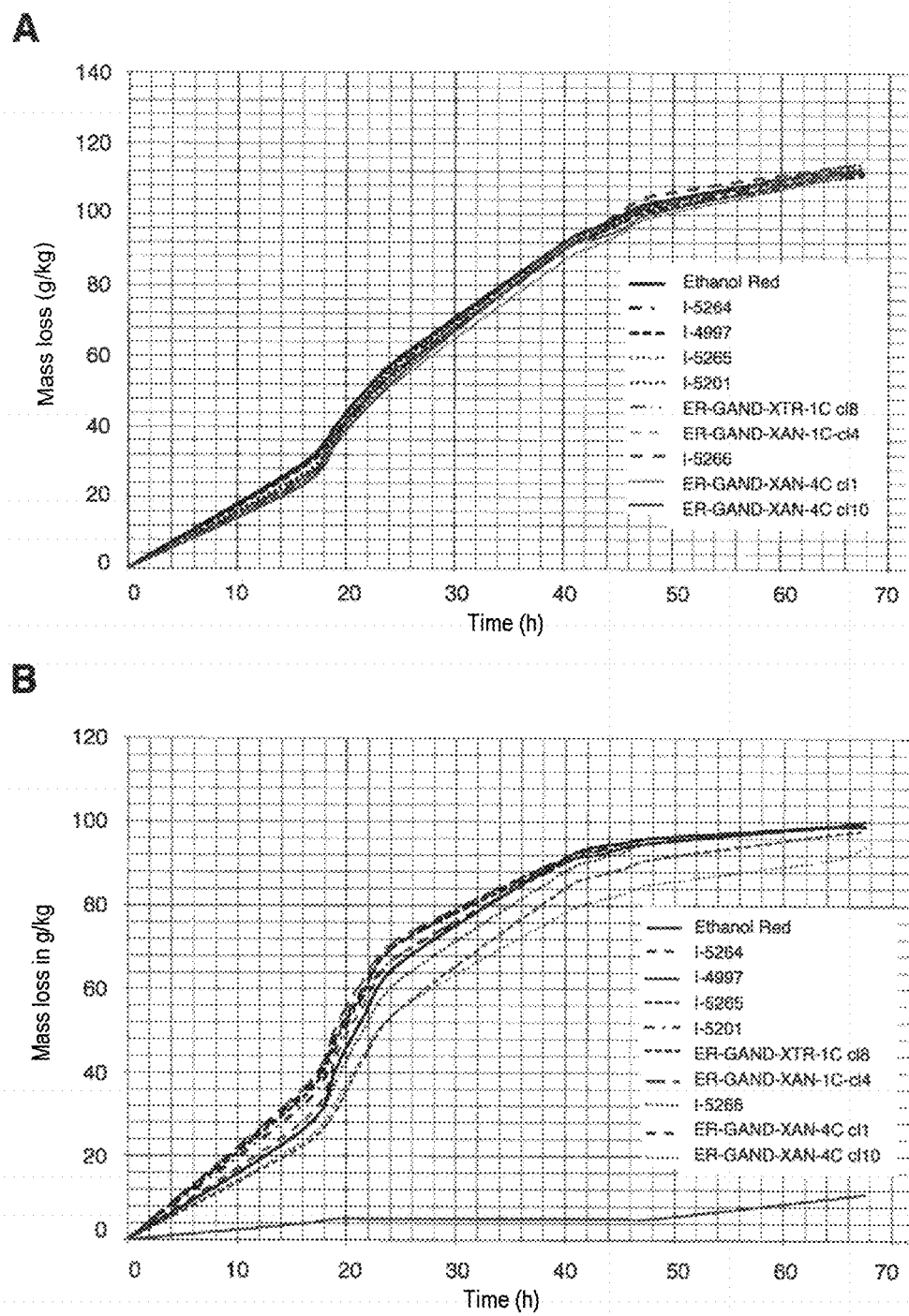
FIG. 1: (A) Mass loss observed for the transformants of the strain deposited in the CNCM under number I-4997 during fermentation in the "Alcohol Max" medium. (B) Mass loss observed for the transformants of the strain number I-4997 during fermentation in the "Dextrin" medium.

As mentioned above, the present invention relates to *Saccharomyces cerevisiae* yeast strains having a high yield in the production of first-generation bioethanol, in particular bioethanol produced from biomass comprising starch.

I—Genetically Modified *Saccharomyces cerevisiae* Strains

A *Saccharomyces cerevisiae* yeast strain according to the present invention is characterized in that it co-expresses:
  a gene encoding a xylanase of fungal origin;
  a gene encoding a glucoamylase of fungal origin; and
  a gene encoding glucoamylase from *Saccharomyces cerevisiae* var. *diastaticus*.

The expression "yeast strain" refers to a relatively homogeneous population of yeast cells. A yeast strain is obtained from a clone, a clone being a population of cells obtained from a single yeast cell. In the context of the present invention, a starting *Saccharomyces cerevisiae* yeast strain is any *Saccharomyces cerevisiae* strain that can be genetically modified to introduce the heterologous xylanase and glucoamylase genes according to the invention. In certain preferred embodiments, the starting *Saccharomyces cerevisiae* strain is a strain known to be useful in bioethanol production, such as for example the *Saccharomyces cerevi-*

*siae* yeasts used by first-generation ethanol producers, which are specialized yeasts allowing the optimization of the profitability of the production process. These yeasts, which are well known to the person skilled in the art, are, inter alia: Ethanol Red® (LEAF), Thermosacc® (Lallemand), Angel Super Alcohol® (Angel) and Fali® (AB Mauri). The expected qualities of these yeasts are their ability to rapidly produce high concentrations of ethanol and to deplete the sugars in the fermentation media over the temperature and pH ranges representative of industrial conditions.

As indicated above, the strains according to the present invention are improved strains compared with *Saccharomyces cerevisiae* yeast strains previously developed by the present Inventors, i.e., compared with *Saccharomyces cerevisiae* yeast strains where the introduction of a gene encoding glucoamylase from *Saccharomyces cerevisiae* var. *diastaticus* and a gene encoding a glucoamylase of fungal origin made it possible to obtain strains with excellent starch hydrolysis capabilities (WO 2017/037362).

As used herein, "gene encoding a glucoamylase" means an amino acid sequence which, when expressed, results in the formation of a functional glucoamylase protein.

As used herein, "glucoamylase" means an enzyme capable of hydrolyzing the α-1,4 glycosidic bonds of crude or soluble starch from the non-reducing end of amylose and amylopectin. Amylases are also known as amyloglucosidases or γ-amylases (Medline reference: EC 3.2.1.3). In addition to acting on the α-1,4-bonds of starch, glucoamylase is capable of slowly hydrolyzing the α-1,6-bonds of amylopectin molecules, provided that the neighboring bond in the sequence is an α-1,4-bond.

The term "glucoamylase of fungal origin" refers to any glucoamylase coming from a fungus and whose corresponding gene can be integrated into the genome of a yeast strain such that expression of the gene results in the formation of a functional glucoamylase protein. In particular, a glucoamylase of fungal origin can be selected from commercial glucoamylases known for their good enzymatic activity. In the context of the present invention, a glucoamylase of fungal origin may be selected from the group consisting of: an *Aspergillus niger* glucoamylase, a *Saccharomycopsis fibuligera* glucoamylase, a *Trichoderma reesei* glucoamylase, a *Rhizopus oryzae* glucoamylase, an *Aspergillus oryzae* glucoamylase and a *Thermomyces lanuginosus* glucoamylase. These glucoamylases are known to the skilled person, and their sequences are accessible under the following GenBank numbers (www.ncbi nlm nih.gov/genbank/): *Trichoderma reesei* (ETS06561), *Rhizopus oryzae* (BAA00033), *Aspergillus oryzae* (BAA00841), *Thermomyces lanuginosus* (AB Q23180).

In certain particular embodiments, the glucoamylase of fungal origin is an *Aspergillus niger* or *Saccharomycopsis fibuligera* glucoamylase. *Aspergillus niger* glucoamylase is encoded by the GLAA gene which has the nucleic sequence SEQ ID NO: 1, and has the protein sequence SEQ ID NO: 2. *Saccharomycopsis fibuligera* glucoamylase is encoded by the GLU0111 gene which has the nucleic sequence SEQ ID NO: 9, and has the protein sequence SEQ ID NO: 10.

Glucoamylase from *Saccharomyces cerevisiae* var. *diastaticus* is encoded by the STA1 gene which has the nucleic sequence SEQ ID NO: 3, and has the protein sequence SEQ ID NO: 4.

In certain embodiments, a *Saccharomyces cerevisiae* yeast strain according to the invention is characterized in that it co-expresses:

a gene encoding a xylanase of fungal origin;
a gene encoding a glucoamylase from *Aspergillus niger*; and
a gene encoding glucoamylase from *Saccharomyces cerevisiae* var. *diastaticus*. Thus, for example, such a *Saccharomyces cerevisiae* strain can be characterized in particular in that it contains the nucleic sequence SEQ ID NO: 1 and the nucleic sequence SEQ ID NO: 3. Alternatively or additionally, such a *Saccharomyces cerevisiae* strain can be characterized in particular in that the glucoamylase from *Saccharomyces cerevisiae* var. *diastaticus* has the protein sequence SEQ ID NO: 4 and the glucoamylase from *Aspergillus niger* has the protein sequence SEQ ID NO: 2.

A *Saccharomyces cerevisiae* yeast strain according to the invention differs from the *Saccharomyces cerevisiae* strain previously developed by the present Inventors (WO 2017/037362) in that in addition to the gene encoding a glucoamylase of fungal origin; and the gene encoding glucoamylase from *Saccharomyces cerevisiae* var. *diastaticus*, it also co-expresses a gene encoding a xylanase of fungal origin.

As used herein, "gene encoding a xylanase" means an amino acid sequence which, when expressed, results in the formation of a functional xylanase protein.

As used herein, "xylanase" means a glycoside hydrolase enzyme that hydrolyses the bonds (1→4)-β-D-xylosidic bonds in xylans, thus generating xylose. Xylanases are also known as endo-1,4-β-xylanases (Medline reference: EC 3.2.1.8). These enzymes are involved in the degradation of hemicellulose, one of the main constituents of cell walls in plants. They are produced in particular by fungi, bacteria, yeasts, marine algae, protozoa, snails, crustaceans, insects and certain seeds, but not by mammals.

In the context of the presence of the invention, xylanase is a xylanase of fungal origin. The term "xylanase of fungal origin" refers to any xylanase coming from a fungus and whose corresponding gene can be integrated into the genome of a yeast strain in such a way that expression of the gene results in the formation of a functional xylanase protein. In particular, a xylanase of fungal origin can be selected from commercial xylanases known for their good enzymatic activity. In the context of the present invention, a xylanase of fungal origin can be selected from the group consisting of: *Aspergillus niger* xylanase, *Aspergillus awamori* xylanase, *Aspergillus tubingensis* xylanase, *Aspergillus nidulans* xylanase, and *Trichoderma reesei* xylanase. These xylanases are known to the skilled person, and their sequences are accessible under the following GenBank numbers (www.ncbi.nlm.nih.gov/genbank/): *Aspergillus niger* (FJ785738), *Aspergillus awamori* (X78115), *Aspergillus tubingensis* (L26988), *Aspergillus nidulans* (Z49892), and *Trichoderma reesei* (X69573).

In certain particular embodiments, the xylanase of fungal origin is an *Aspergillus niger* or *Trichoderma reesei* xylanase. *Aspergillus niger* xylanase is encoded by the XYN1 gene which has the consensus nucleic sequence SEQ ID NO: 5, and has the protein sequence SEQ ID NO: 6. *Trichoderma reesei* xylanase is encoded by the XYN2 gene which has the consensus nucleic sequence SEQ ID NO: 7, and has the protein sequence SEQ ID NO: 8.

The expressions "glucoamylase of fungal origin" and "glucoamylase from *Saccharomyces cerevisiae* var. *diastaticus*" should not be interpreted strictly: they encompass glucoamylases of fungal origin and from *Saccharomyces cerevisiae* var. *diastaticus* which are encoded by the nucleic sequences as described above, but also functional variants of these glucoamylases. Similarly, the term "xylanase of fungal origin", as used herein, encompasses xylanases of fungal origin which are encoded by the nucleic sequences as described above, but also functional variants of these xylanases.

Typically, a functional variant of a glucoamylase or xylanase according to the invention has a protein sequence having a percentage identity of at least 80%, 90%, or 95%, more particularly 99%, with the protein sequence of said glucoamylase or xylanase, respectively. For example, functional variants of *Aspergillus niger* glucoamylase have a protein sequence having at least 80%, at least 90%, or at least 95%, more particularly at least 99% identity with the sequence SEQ ID NO: 2; functional variants of the glucoamylase from *Saccharomyces cerevisiae* var. *diastaticus* glucoamylase have a protein sequence with at least 80%, at least 90%, or at least 95%, more particularly at least 99% identity with the sequence SEQ ID NO: 4; functional variants of *Aspergillus niger* xylanase have a protein sequence with at least 80%, at least 90%, or at least 95%, more particularly at least 99% identity with the sequence SEQ ID NO: 6; and functional variants of *Trichoderma reesei* xylanase have a protein sequence having at least 80%, at least 90%, or at least 95%, more particularly 99% identity with the sequence SEQ ID NO: 8.

The "percent identity" is a comparison between amino acid sequences, and is determined by comparing two sequences optimally aligned on a comparison window. The skilled person knows how to calculate a percent identity between two sequences and has many tools at her disposal to do so. One of the two sequences may have insertions, substitutions and deletions of amino acids relative to the other sequence.

It is within the skills of the skilled person to select functional variants of glucoamylases and xylanases according to the invention. "Functional variant of a glucoamylase" means a variant that retains the enzymatic activity of the glucoamylase and this with similar starch hydrolysis kinetics characteristics. "Functional variant of a xylanase" means a variant that retains the enzymatic activity of xylanase with similar xylan hydrolysis kinetics. Methods for measuring and comparing starch hydrolysis kinetics and xylan hydrolysis kinetics are described in the experimental part of the present application (see also WO 2017/037362).

The strains according to the invention can be generated by any appropriate method. The skilled person knows, for example, multiple methods for introducing a gene into a yeast strain, in particular through the use of vectors comprising expression cassettes. "Vector" means any DNA sequence into which foreign nucleic acid fragments can be inserted. Vectors allow foreign DNA to be introduced into a host cell. Examples of vectors are plasmids, cosmids, virus-derived vectors. Vectors allow either the integration of heterologous genes directly into the yeast genome or their expression in an independent plasmid. The introduction of vectors into a host cell is a process widely known to the skilled person. Several methods are notably described in "Current Protocols in Molecular Biology", 13.7.1-13.7.10; or in Ellis et al., Integrative Biology, 2011, 3(2), 109-118.

Genetic modifications according to the invention may be carried out simultaneously or sequentially. Thus, for example, in certain embodiments, a *Saccharomyces cerevisiae* strain according to the invention is prepared from a *Saccharomyces cerevisiae* strain previously developed by the present Inventors and described in WO2017/037362 (i.e., from a strain already containing a gene encoding a glucoamylase of fungal origin and a gene encoding a glucoamylase from *Saccharomyces cerevisiae* var. *diastaticus*). Alternatively, in other embodiments, a *Saccharomyces cerevisiae* strain according to the invention is prepared by integrating the three genes in a *Saccharomyces cerevisiae* strain such as, for example, a specialized strain—see above. In these embodiments, the gene encoding a glucoamylase of fungal origin, the gene encoding glucoamylase from *Saccharomyces cerevisiae* var. *diastaticus*, and the gene encoding a xylanase of fungal origin can be inserted within one and the same vector, or within two or three separate vectors. A suitable vector may be a plasmid.

In the context of the present invention, a vector used to introduce a gene into a *Saccharomyces cerevisiae* strain may contain a selection marker. "Selection marker" means a gene the expression of which confers on the yeasts containing it a characteristic enabling them to be selected. It may be for example a gene for antibiotic resistance or a gene allowing the yeast to grow in a particular medium.

In a vector, a (glucoamylase or xylanase) gene according to the invention is generally operably linked to a promoter, a terminator and/or any other sequence necessary for its expression in yeast. The terms "operably linked" and "linked in an operable manner" are used interchangeably and refer to a functional link between the elements allowing the expression of the gene and optionally its regulation (5' and 3' regulatory sequences) and the sequence of the reporter gene they control. The skilled person knows how to select the promoters, terminators and other sequences necessary for the expression of a gene in *Saccharomyces cerevisiae* yeast.

In certain particular embodiments of the invention, the expression of a (glucoamylase and/or xylanase) gene is controlled by a so-called "strong" promoter (i.e., a promoter with a high transcriptional potential so that the gene is strongly expressed). In the context of the present invention, a strong promoter is for example the pADH1 promoter, the pTEF promoter, or the pTDH3 promoter.

A *Saccharomyces cerevisiae* yeast strain according to the invention may comprise multiple copies of at least one of the glucoamylase genes of fungal origin, from *Saccharomyces cerevisiae* var. *diastaticus*, and xylanase genes of fungal origin. In general, a *Saccharomyces cerevisiae* strain according to the invention comprises, m copies of the gene encoding xylanase of fungal origin; n copies of the gene encoding glucoamylase of fungal origin; and p copies of the gene encoding glucoamylase from *Saccharomyces cerevisiae* var. *diastaticus*, wherein m is an integer comprised between 1 and 10, n is an integer comprised between 2 and 10, and p is an integer comprised between 2 and 10. Thus, n and p can independently be equal to 2, 3, 4, 5, 6, 7, 8, 9, or 10 and m can be equal to 1, 2, 3, 4, 5, 6, 7, 8, 9, or 10. In certain particular embodiments, m is equal to 1 or 4. In the same, or other, particular embodiments, n is equal to 6 and p is equal to 4.

The invention relates to in particular the *Saccharomyces cerevisiae* yeast strain which was deposited, by the present Applicant, in the CNCM (Collection Nationale de Cultures de Microorganismes, Institut Pasteur, 25-28 rue du Docteur Roux, 75 724 Paris Cedex 15), under the Budapest Treaty, under number I-5201 on 26 Apr. 2017. This strain comprises 6 copies of the *Aspergillus niger* glucoamylase gene, 4 copies of the *Saccharomyces cerevisiae* var. *diastaticus* glucoamylase gene and 1 copy of the *Aspergillus niger* xylanase gene.

II—Method for Obtaining Genetically Modified *Saccharomyces cerevisiae* Strains Useful for Bioethanol Production The present Inventors have, in parallel, developed a method for obtaining *Saccharomyces cerevisiae* strains useful in bioethanol production. The method comprises the steps consisting in:

(a) genetically modifying a *Saccharomyces cerevisiae* yeast so that it co-expresses a gene encoding a xylanase of fungal origin, a gene encoding a glucoamylase of fungal origin, and a gene encoding glucoamylase from *Saccharomyces cerevisiae* var. *diastaticus* or obtaining such a *Saccharomyces cerevisiae* yeast;

(b) culturing and fermenting the yeast of step (a) on a synthetic dextrin medium; and (c) selecting at least one strain exhibiting fermentation kinetics in the synthetic dextrin medium at least equal to or greater than the fermentation kinetics of the *Saccharomyces cerevisiae* strain deposited on 9 Jul. 2015 in the CNCM under number I-4997.

As the skilled person will recognize, after the genetic modification step (a), it is preferable to select the clones that have correctly integrated the introduced genes. Thus, the yeast of step (a) that is used in step (b) is a clone that has correctly integrated the gene encoding xylanase of fungal origin, the gene encoding glucoamylase of fungal origin, and the gene encoding glucoamylase from *Saccharomyces cerevisiae* var. *diastaticus*. The skilled person knows how to select such clones, for example by using a selection marker introduced into the starting *Saccharomyces cerevisiae* yeast. The Examples provided in the present document describe an example of a method for selecting clones. In this example, a clone obtained in step (a) is cultured in a rich medium (nutrient-rich, YPG type medium), then the culture supernatant is transferred to a minimum medium containing xylan as carbon source. A second yeast, CelluX™ yeast (which was deposited by the Applicant on 12 Dec. 2013 in the CNCM under number I-4829), is added to the reaction medium. A clone is selected (i.e., identified as having correctly integrated the introduced genes), if the CelluX™ strain grows.

As will be recognized by the skilled person, the *Saccharomyces cerevisiae* yeast strain obtained in step (a) of the method described above is a strain according to the present invention. Its characteristics are therefore identical to those described in the preceding section.

The skilled person knows how to conduct a fermentation reaction of such a *Saccharomyces cerevisiae* yeast on a synthetic dextrin medium (step (b)), and determine the optimal conditions for fermentation. As used herein, "synthetic dextrin medium" means a cell culture medium, preferably a yeast cell culture medium, containing dextrins, as known to the skilled person. It is for example a culture medium containing starch dextrins (220 g/kg), yeast extract (5 g/kg), urea (2 g/kg), potassium dihydrogen phosphate (1 g/kg) as well as minerals and vitamins (such as vitamin B1 and vitamin B6).

In step (c), the selection of a *Saccharomyces cerevisiae* strain that is efficient and useful in bioethanol production is done by comparing its fermentation kinetics with that of the *Saccharomyces cerevisiae* strain deposited, by the present Applicant on 9 Jul. 2015 in the CNCM under number I-4997. Fermentation kinetics can be easily measured by various techniques known to the skilled person. For example, fermentation kinetics can be measured through fermentation monitoring by weighing over time.

Strain I-4997, which serves as the reference, is one of the strains previously developed by the present Inventors and described in WO 2017/037362. *Saccharomyces cerevisiae* strain I-4997 contains at least 4 copies of the gene encoding the *Aspergillus niger* glucoamylase and at least 3 copies of the gene encoding the *Saccharomyces cerevisiae* var. *diastaticus* glucoamylase.

A strain selected by a method according to the present invention therefore necessarily presents fermentation properties identical or superior to the *Saccharomyces cerevisiae* strain I-4997, in a synthetic dextrin medium. Consequently, the present Inventors have also developed a method for increasing the bioethanol production yield of a *Saccharomyces cerevisiae* yeast strain.

III—Method for Increasing the Bioethanol Production Yield of a *Saccharomyces cerevisiae* Strain The present invention therefore also relates to a method for increasing the bioethanol production yield of a *Saccharomyces cerevisiae* yeast strain, said method comprising the steps consisting in:

(a) providing (or obtaining) a *Saccharomyces cerevisiae* yeast co-expressing a gene encoding a glucoamylase of fungal origin, and a gene encoding glucoamylase from *Saccharomyces cerevisiae* var. *diastaticus*;

(b) genetically modifying the yeast of step (a) so that it also expresses a gene encoding a xylanase of fungal origin;

(c) culturing and fermenting the yeast obtained in step (b) on a synthetic dextrin medium; and (d) selecting at least one strain with fermentation kinetics in the synthetic dextrin medium at least equal to or greater than the fermentation kinetics of the strain deposited on 9 Jul. 2015 in the CNCM under number I-4997.

The strain of step (a) can be any *Saccharomyces cerevisiae* strain co-expressing a gene encoding a glucoamylase of fungal origin, and a gene encoding glucoamylase from *Saccharomyces cerevisiae* var. *diastaticus*. In certain embodiments, the glucoamylase of fungal origin is selected from the group consisting of: *Aspergillus niger* glucoamylase, *Saccharomycopsis fibuligera* glucoamylase, *Trichoderma reesei* glucoamylase, *Rhizopus oryzae* glucoamylase, *Aspergillus oryzae* glucoamylase, and *Thermomyces lanuginosus* glucoamylase as described above. In some particular embodiments, the glucoamylase of fungal origin whose exogenous gene is present in the *Saccharomyces cerevisiae* strain of step (a) is an *Aspergillus niger* glucoamylase, for example an *Aspergillus niger* glucoamylase encoded by the nucleic sequence SEQ ID NO: 1 or an *Aspergillus niger* glucoamylase consisting of the polypeptide sequence SEQ ID NO: 2 or a functional variant of the polypeptide sequence SEQ ID NO: 2. In the same or other particular embodiments, the *Saccharomyces cerevisiae* var. *diastaticus* glucoamylase whose exogenous gene is present in the *Saccharomyces cerevisiae* strain of step (a) is a *Saccharomyces cerevisiae* var. *diastaticus* glucoamylase encoded by the nucleic sequence SEQ ID NO: 3 or a *Saccharomyces cerevisiae* var. *diastaticus* glucoamylase consisting of the polypeptide sequence SEQ ID NO: 4 or a functional variant of the polypeptide sequence SEQ ID NO: 4.

In certain particular embodiments, the strain of step (a) is a *Saccharomyces cerevisiae* strain co-expressing a gene encoding a glucoamylase of fungal origin, and a gene encoding glucoamylase from *Saccharomyces cerevisiae* var. *diastaticus*, as described in WO 2017/037362. For example, the strain of step (a) is the *Saccharomyces cerevisiae* yeast strain deposited, by the present Applicant, on 9 Jul. 2015 in the CNCM under number I-4997.

The genetic modification step (b) may be carried out by any method known to the skilled person, as noted above.

As indicated above, after genetic modification step (b), a selection can be made of clones that have correctly integrated the gene encoding xylanase of fungal origin, for example by using a selection marker.

Steps (c) and (d) of the method for increasing the bioethanol production yield of a *Saccharomyces cerevisiae* yeast strain can be carried out as indicated for the selection method according to the invention.

The invention also relates to any yeast strain obtained by a method of selection or yield increase according to the invention. The invention also relates to a yeast obtained by culturing one of the strains of the invention. The processes for culturing a yeast strain are known in the art, and the skilled person knows how to optimize the culture conditions for each strain according to its nature.

The yeast strains of the invention and the yeasts obtained by culturing these strains are of particular interest for producing bioethanol from biomass, in particular from biomass containing starch.

IV—Use of Genetically Modified *Saccharomyces cerevisiae* Strains for Bioethanol Production The present invention therefore relates to the use of a *Saccharomyces cerevisiae* strain according to the present invention for the production of bioethanol from a biomass containing starch. The present invention also relates to a method for producing bioethanol from a biomass containing starch, said method comprising the steps consisting in:

(a) pre-hydrolyzing (i.e., partially hydrolyzing) and liquefying the starch from the biomass;

(b) reacting the biomass containing the pre-hydrolyzed and liquefied starch obtained in step (a) with a *Saccharomyces cerevisiae* yeast strain according to the present invention to produce bioethanol; and (c) extracting the bioethanol produced in step (b).

As used herein, the term "biomass" refers to all organic matter of plant origin that can become a source of energy after processing. Preferably, in the context of the invention, the biomass is derived from agricultural or agri-food products and/or co-products. For example, a biomass can be derived from corn, wheat, barley, rye, sorghum, cassava, triticale, potato, sweet potato, sugar cane, sugar beet, sugar sorghum. In the context of the present invention, the biomass contains starch. Biomasses rich in starch may be selected, or may be derived from, for example, grains of corn, barley, wheat, cassava, potato tubers, etc.

Steps (a), (b) and (c) of the method according to the invention can be carried out as in the case of a conventional bioethanol production process. Such steps are known to the skilled person.

The invention applies particularly to the production of bioethanol as fuel, but also to the production of bioethanol for the food, chemical, pharmaceutical and cosmetic industries.

Unless otherwise defined, all technical and scientific terms used in the Description have the same meaning as that commonly understood by an ordinary specialist in the field to which the invention belongs. Similarly, all publications, patent applications, patents and other references mentioned herein are incorporated by reference.

EXAMPLES

The following examples describe certain embodiments of the present invention. However, it is understood that the examples and figures are presented by way of illustration only and in no way limit the scope of the invention.

Example 1: Obtaining and Characterizing Transformants of Strain I-4997 Containing 1 Or 4 Copies of a Gene Encoding Xylanase from *Aspergillus Niger* (XYN1) or a Gene Encoding Xylanase From *Trichoderma Reesei* (XYN2)

The strategy used to clone a xylanase activity in *Saccharomyces cerevisiae* strain ER-GAND-8159-C1 (i.e., the strain deposited, by the Applicant, on 9 Jul. 2015 in the CNCM under number I-4997) is based on the use of a multi-integrative expression system. With this system, it is possible to simultaneously integrate one or more copies of a gene encoding a given xylanase at a given locus. The Inventors chose to integrate 1 copy or 4 copies of one of the two genes XYN1 from *Aspergillus niger* and XYN2 from *Trichoderma reesei* in order to measure a possible effect related to the copy number on xylanase activity.

A. Obtaining Expression Plasmids

Xylanase from *Aspergillus niger* (XYN1). The XYN1 gene encoding *Aspergillus niger* xylanase was previously amplified by PCR using genetic material derived from *Aspergillus niger* strain ATCC10577. The PCR product was then cloned into an expression vector (developed in-house) under the dependence of a strong pADH1 promoter and the tCYC1 terminator. The resulting plasmid then serves as a template for the generation of expression modules, as described in paragraph B below.

Xylanase from *Trichoderma reesei* (XYN2). The *Trichoderma reesei* xylanase that was used is encoded by the XYN2 gene. The sequence used is the cDNA version, stripped of its introns and optimized through codons to improve the translation of the protein in the *Saccharomyces cerevisiae* yeast. The plasmid which has the XYN2 gene dependent on the pADH1/tCYC1 pair, was used as PCR template to synthesize the expression modules.

B. Obtaining the Expression Modules

The strategy employed by the Inventors consisted in simultaneously integrating several xylanase gene expression modules into a *Saccharomyces cerevisiae* strain in a single step at a given locus, based on the yeast's natural ability to carry out homologous recombination in vivo. The Inventors have defined the PCR primers to be used to integrate the modules at the BUD5 locus. Depending on the strains developed, 1 or 4 *A. niger* xylanase or *T. reesei* xylanase expression modules, as well as a selection module were integrated.

Each amplified module has recombinogenic sequences (A1, B1, C1 and D1) on either side of its promoter and terminator. These sequences are provided by the floating tails of the PCR primers (Table 1) and allow the modules to specifically align and recombine by homology between these recombinogenic sequences.

The presence of sequences homologous to a given locus, for example the BUD5 locus, at the 5' and 3' ends of the multi-integrative expression cassette allows the simultaneous integration of the expression modules and the homologous recombination selection module at this given locus.

C. Obtaining and Selecting Transformants

Obtaining Transformants. For each construct, the different modules (see Table 2) were equimolarly mixed in order to integrate at the BUD5 locus of strain I-4997, 1 or 4 copies of *A. niger* or *T. reesei* xylanases as well as a selection module.

The selection of clones having correctly integrated the expression modules is initially made on the basis of the presence of the selection module in the integration cassette. The selection module comprises a strong promoter/terminator pair and a gene the expression os which confers on the yeasts containing it a characteristic enabling them to be selected on a given medium. The Inventors thus isolated the clones derived from each transformation.

secreting an active xylanase have the ability to hydrolyze the xylan from the medium to xylose. After this first step of transformant growth, an inoculum of CelluX™, a yeast capable of consuming xylose, was added to each well. The wells in which CelluX™ growth is observed are identified as containing a clone secreting xylanase activity. This approach makes it possible to identify transformants exhibiting the desired phenotype. To this end, the optical density (OD at 600 nm) of the cultures is measured at the end of growth.

(b) Validation of Selected Transformants by PCR. Before evaluation in fermentation, the genotype was verified for 2 transformants per construct among those identified as exhibiting a [Xylanase]+ phenotype. A panel of PCR reactions, aimed at confirming the presence of the different genes theoretically present in the constructs obtained, was performed on the genomic DNA of the selected transformants.

D. Phenotypic Characterization (Xylanase Activity) of Selected Clones

Solid Phenotype Test. In this test, 5 µL of culture supernatant (5% YPG, 30° C., 24 hours, 150 rpm) was deposited on a medium containing birch xylan, and the hydrolysis halos of the xylan were visualized after staining with 1% Congo Red and destaining with 1 M NaCl. Hydrolysis halos were observed for all clones considered.

Liquid Phenotype Test. This phenotypic characteristic is based on the same principle as that used for the selection of transformants (see above). In this test, 5 µL of cultured supernatant (5% YPG) was incubated at 50° C. overnight in the presence of birch xylan (vol/vol), then the mixture was inoculated with a suspension calibrated at $OD_{600\ nm}=0.05$ of

TABLE 1

Listing of Primers Used and Nomenclature of Synthesized Expression Modules.

| | Sense (F) and antisense (R) oligonucleotides | Module |
|---|---|---|
| Selection gene | (F): CGCTCCAGAATTAGCGGACCTCTTGAGCGGTGAGCCTCTGGCAAA GAAGAGCATAACCGCTAGAGTACTT (SEQ ID NO: 11)<br>(R): TCACTGTACGGTGAGAACGTAGATGGTGTGCGCATAGGCCACTAG TGGATCT (SEQ ID NO: 12) | M0 |
| A. niger XYN1 gene | (F): CACACCATCTACGTTCTCACCGTACAGTGAGCATAACCGCTAGAG TACTT (SEQ ID NO: 13)<br>(R): CTCAAGAACGTAGGACGATAACTGGTTGGAAAGCGTAAACACGGA GTCAACAGCTTGCAAATTAAAGCCT (SEQ ID NO: 14) | M5-AN |
| | (F): SEQ ID NO: 13<br>(R): TTACGTAGACTGAGTAGCAACGGTTGAGGACAGCTTGCAAATTAA AGCCT (SEQ ID NO: 15) | M6-AN |
| | (F): TCCTCAACCGTTGCTACTCAGTCTACGTAAGCATAACCGCTAGAG TACTT (SEQ ID NO: 16)<br>(R): TCAGTAGCACAGAGAAGTGTAGGAGTGTAGCAGCTTGCAAATTAA AGCCT (SEQ ID NO: 17) | M7-AN |
| | (F): CTACACTCCTACACTTCTCTGTGCTACTGAGCATAACCGCTAGAG TACTT (SEQ ID NO: 18)<br>(R): TTAGGATACATGCAGTAGACGAGGTAAGCACAGCTTGCAAATTAA AGCCT (SEQ ID NO: 19) | M8-AN |
| | (F): TGCTTACCTCGTCTACTGCATGTATCCTAAGCATAACCGCTAGAG TACTT (SEQ ID NO: 20)<br>(R): SEQ ID NO: 14 | M9-AN |
| T. reesei XYN2 gene | (F): SEQ ID NO: 13<br>(R): SEQ ID NO: 14 | M5-TR |
| | (F): SEQ ID NO: 13<br>(R): SEQ ID NO: 15 | M6-TR |
| | (F): SEQ ID NO: 16<br>(R): SEQ ID NO: 17 | M7-TR |
| | (F): SEQ ID NO: 18<br>(R): SEQ ID NO: 19 | M8-TR |
| | (F): SEQ ID NO: 20<br>(R): SEQ ID NO: 14 | M9-YR |

TABLE 2

Mixing of modules before transformation of strain 1-4997.

| Copy number | Modules used | Strains obtained |
|---|---|---|
| 1 copy of A. niger XYN1 | M0<br>M5-AN | ER-GAND-XAN |
| 4 copies of A. niger XYN1 | M0<br>M6-AN<br>M7-AN<br>M8-AN<br>M9-AN | ER-GAND-XAN-4C |
| 1 copy of T. reesei XYN2 | M0<br>M5-TR | ER-GAND-XTR1C |
| 1 copy of T. reesei XYN2 | M0<br>M6-TR<br>M7-TR<br>M8-TR<br>M9-TR | ER-GAND-XTR-4C |

Selection of Transformants.

(a) Functional Screening in relation to Xylanase Activity. The screening of the transformants obtained was carried out in 2 steps. First, the transformants obtained were cultured in a minimum medium containing birch xylan. Indeed, clones CelluX™. Samples, taken before and after inoculation with CelluX™, were analyzed by HPLC to determine the concentration of xylose during CelluX™ cell growth.

The results obtained in the phenotypic test in liquid medium confirmed the correlation between CelluX™ growth and xylose consumption for the clones considered.

TABLE 3

Determination of Xylose Consumption and Measurement of CelluX ™ Cell Growth for Selected Transformants.

| Yeast culture supernatant | Copy no. | Clone no. | Xylose concentration (g/L) | | | CelluX ™ growth OD (600 nm) | | |
|---|---|---|---|---|---|---|---|---|
| | | | T0 | Tf | Reduction (%) | T0 | Tf | Multiplier Coefficient |
| ER-GAND-XAN | 1 | cl1 | 0.32 | 0.03 | −92% | 0.05 | 2.2 | 44 x |
| | | cl4 | 0.19 | 0.08 | −59% | 0.05 | 0.8 | 16 x |
| | 4 | cl1 | 0.26 | 0.03 | −89% | 0.05 | 1.5 | 30 x |
| | | cl9 | 0.21 | 0.03 | −87% | 0.05 | 1.5 | 30 x |
| ER-GAND-TR | 1 | cl3 | 0.22 | 0.08 | −62% | 0.05 | 0.9 | 18 x |
| | | cl8 | 0.18 | 0.03 | −81% | 0.05 | 1.1 | 22 x |
| | 4 | cl2 | 0.23 | 0.03 | −88% | 0.05 | 1.9 | 38 x |
| | | cl10 | 0.42 | 0.06 | −87% | 0.05 | 1.2 | 24 x |
| ER-GAND-8159[a] | | control | 0.16 | 0.03 | −79% | 0.05 | 0.4 | 8 x |
| | | + sXYN[b] | 3.59 | 0.23 | −93% | 0.05 | 2.9 | 58 x |
| Ethanol Red ® [c] | | control | 0.14 | 0.06 | −56% | 0.05 | 0.4 | 8 x |
| | | + sXYN | 3.52 | 0.25 | −93% | 0.05 | 2.9 | 58 x |

[a]ER-GAND-8159 is the strain deposited in the CNCM under number I-4997.
[b]sXYN = 12 U/μL T. reesei xylanase solution
[c] Ethanol Red ® is a strain deposited in the CNCM on 4 Sep. 2008, by the present Applicant, under number I-4071.

E. Evaluation of Selected Clones in Fermentation

Determination of Performance with respect to Ethanol Production in "Alcohol Max" Medium (YFAM). In order to determine whether the integration of the expression modules of *A. niger* xylanase and *T. reesei* xylanase had an impact on the transformants' ability to produce ethanol, they were characterized in a so-called "alcohol max" medium containing 280 g/kg sucrose (see composition below), which makes it possible to measure their ethanol production potential under given evaluation conditions.

The "Alcohol Max" medium contains: 280 g/kg sucrose, 5 g/kg yeast extract, 4.7 g/kg di-basic ammonium phosphate (D.A.P.), 11.5 g/kg citric acid, 13.5 g/kg sodium citrate, as well as minerals and vitamins.

The monitoring of mass losses did not reveal any negative impact of the integration of the "xylanase" expression modules on the maximum alcohol production potential of the transformants, either from a kinetic point of view or as an end point, with the exception of clone 1 which has 4 copies of the *A. niger* XYN1 gene which is very slightly impacted at the kinetics level (see FIG. 1(A)).

Fermentation in Dextrin medium. In order to determine whether the selected transformants retained their ability to degrade starch via the production of glucoamylase, the transformants were evaluated in a dextrin medium. Indeed, the strain used as host to integrate the xylanase expression modules corresponds to the ER-GAND-8159 strain (CNCM I-4997) which has 2 glucoamylase genes of different origin. Dextrins are molecules resulting from the hydrolysis of starch, the clones secreting glucoamylases are able to degrade them to glucose and thus produce ethanol. The fermentation conditions used were identical to those used with the YFAM medium.

"Dextrin medium" means a synthetic medium containing dextrins, as known to the skilled person. It is for example a synthetic medium containing starch dextrins (220 g/kg), yeast extract (5 g/kg), urea (2 g/kg), potassium dihydrogen phosphate (1 g/kg) as well as minerals and vitamins.

All clones tested in the dextrin fermentation medium retained their ability to degrade starch when compared with Ethanol Red® which was only able to ferment the glucose initially present in the medium (of the order of 10 g/L) (see FIG. 1(B)). It is also noted that the ER-GAND-XTR-4c c110 clone, which has 4 copies of the XYN2 gene which encodes the *T. reesei* xylanase, and the clone ER-GAND-XTR-1c c18, which has 1 copy of this gene, and to a lesser extent the clone ER-GAND-XTR-4c c12, which has 4 copies of this gene, are negatively impacted in their mass loss kinetics compared with the ER-GAND-8159 control, which is not the case for the ER-GAND-XTR-1c c13 clone (CNCM I-5265) with a single copy of XYN2, for which the mass loss is faster over the first 24 hours and identical to the control over the 40 hours of fermentation that follow. These results suggest an effect related to the clone considered more than they demonstrate a genuine negative impact of the integration of the XYN2 gene.

On the other hand, the four ER-GAND-XAN transformants tested that possess either 1 copy or 4 copies of the XYN1 gene (*A. niger*) have significantly improved mass loss production kinetics over the first 24 hours compared with the ER-8159-GAND-8159 control (CNCM I-4997).

Four transformants were deposited in the CNCM: strain ER-GAND-XAN-1C c11 deposited on 26 Apr. 2017 in the CNCM under accession number I-5201, strain ER-GAND-XAN-4C c19 deposited on 20 Dec. 2017 in the CNCM under accession number I-5264, strain ER-GAND-XTR-1C c13 deposited on 20 Dec. 2017 in the CNCM under accession number I-5265, and strain ER-GAND-XTR-4C c12 deposited on 20 Dec. 2017 in the CNCM under accession number I-5266.

F. Conclusion

The study described in this Example made it possible to obtain transformants of the ER-GAND-8159 strain. These transformants possess 1 copy or 4 copies of *Aspergillus niger* or *Trichoderma reesei* xylanase genes, using the strategy of single-step multi-copy integration by obtaining specifically designed expression modules. Second, the Inventors focused on validating, by PCR, the genotype of the transformants obtained as well as their xylan hydrolysis phenotype, and ensured that their ethanol production and starch hydrolysis capacities had not been negatively impacted by the genetic modifications performed.

Example 2: Evaluation of the Fermentation Performance of Strains on a Bioethanol Production Substrate A. Preparation of a Corn Hydrolysate for Evaluation of Strains Exhibiting Xylanase Activity.

In order to implement the strains generated in this study, a fermentation medium for bioethanol production was prepared. This medium is defined to be close to the market substrates using corn. To this end, corn grits ("Crème de Maïs"-MQ-FT-19, Moulons Waast) were suspended in order to obtain a mixture with about 30% dry matter in water. The pH of this suspension was then adjusted to 6 using a 40% potassium hydroxide solution, and an α-amylase type enzyme (Liquozyme SC-DS, Novozymes) was added at a rate of 0.85 mL enzyme per kg of mobilized grits. A liquefaction heat treatment was then applied to the suspension for 3 hours at 85° C. A typical composition of sugars released after heat treatment is shown in Table 4 below (measured dry matter: 29.1%).

TABLE 4

Composition of Sugars Available
in the Liquefied Substrate.

| Sugars | Concentrations (g/kg) |
|---|---|
| Maltose | 23.9 |
| Glucose | 6.3 |
| Fructose | 0.7 |
| Glycerol | 0.3 |

The liquefied substrate has a total glucose potential measured by the enzymatic method of 226 $g_{glucose}/kg_{substrate}$.

B. Evaluation of the Ethanol Production Performance of Strains Modified by Adding Xylanase Genes Four transformants were tested for their performance in alcoholic fermentation (2 clones incorporating *Aspergillus niger* xylanase, one possessing 1 copy of the gene and the other possessing 4 copies of the gene; and 2 clones each possessing 1 copy of the *Trichoderma reesei* xylanase gene) on the liquefied substrate, compared with the reference strain ER-GAND-8159 (CNCM I-4997).

Preparation of Yeast Creams from the Strains Selected for the Evaluation. Each of the five strains selected for evaluation was cultured on a Petri dish for 24 hours and then stored in the refrigerator before use. Each strain was then collected and used to inoculate 100 mL of acidic medium (for example YM medium) in 250 mL round-bottom flasks. The round-bottom flasks were placed in an incubator at 26° C. for 24 hours.

At the end of this incubation, each medium was centrifuged at 4500 rpm for 5 minutes. After removal of the supernatant, 150 mL of sterile water was added to wash the yeasts. A second centrifugation was then carried out, then after removal of the supernatant, the pellet was taken up in 20 mL of sterile water, homogenized by vortexing and stored cold before being used to inoculate the fermentation test samples.

Performing the Fermentation Tests. For each strain evaluated, 100 g of liquefied substrate was placed in a 250 mL round-bottom flask. An addition of mineral nitrogen was carried out in the form of urea at a rate of 0.5 g nitrogen per kg substrate. The pH was then adjusted to 5 using a 0.5 N sulfuric acid solution. Each strain stored in cream form was then added to the medium at a rate of 0.5 g cream dry matter per kg substrate. Once the strains were added to their respective round-bottom flasks, the tests were placed in an incubator at 32° C. with orbital shaking at 100 rpm.

The monitoring of the tests was carried out by on-line acquisition of the $CO_2$ pressure generated by the fermentation, expressed in equivalent mass loss. At the end of fermentation, the musts were collected and analyzed by HPLC to measure the concentrations of the various biochemical compounds and determine the fermentation balances.

Figure 2:
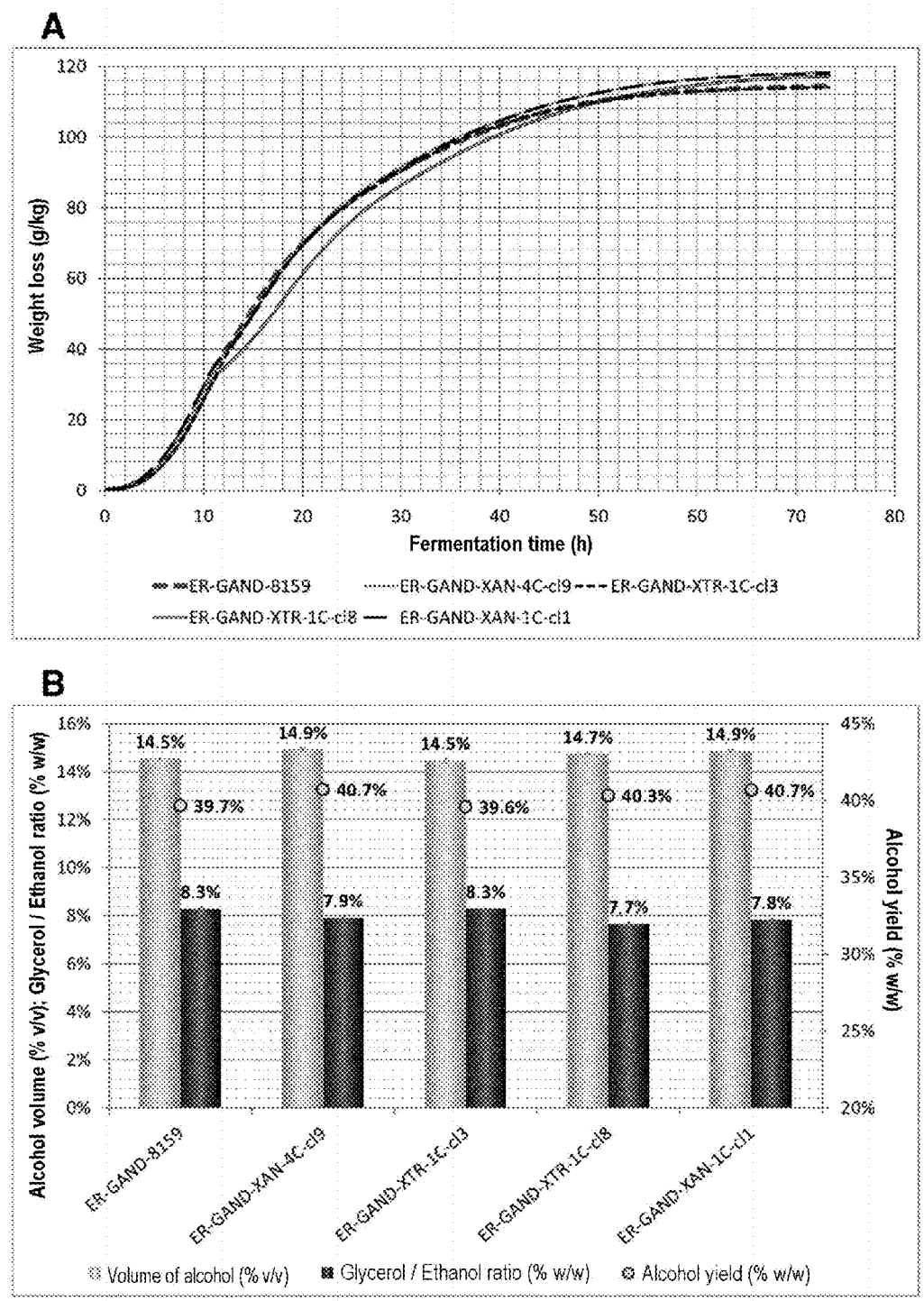
FIG. 2: (A) Comparison of the fermentation kinetics of the different strains studied. (B) Comparison of the values of ethanol content, glycerol/ethanol mass ratios and ethanol yields calculated on the glucose potential of the substrate used for the fermentation of the different strains studied.

Results Obtained. FIG. 2(A) presents the fermentation kinetics observed. It appears that with the exception of the ER-GAND-XTR-1C-c18 strain, which shows a delay in initial kinetics, all strains show a similar onset of fermentation during the first 36 hours of fermentation. After 36 hours, the reference strain ER-GAND-8159 slows down, as does the ER-GAND-XTR-1C-c13 (1-5265) strain with identical kinetics. Both strains expressing the *Aspergillus niger* xylanase gene continue fermentation at a higher rate and produce a higher amount of $CO_2$ during the test. The ER-GAND-XTR-1C-c18 strain that had an initial kinetic delay catches up with the reference at 54 hours of fermentation and exceeds it to finish slightly behind the two ER-GAND-XAN strains.

At the end of fermentation, analyses were carried out to measure the performance gains of the new transformants. FIG. 2(B) shows the values for ethanol content, glycerol/ethanol mass ratio and ethanol yield calculated on the glucose potential of the substrate used.

ER-GAND-XAN transformants are observed to have an advantage over ethanol production (higher titer and higher yield) as well as reduced glycerol production. Concerning the ER-GAND-XTR strains, only clone 8 has an advantage on these same parameters, clone 3 being similar to the reference in terms of performance.

Table 5 below presents all the data collected during the tests to compare performance to the reference. The left side of the table presents the raw values and the right side presents the gain observed relative to the reference.

Figure 3:
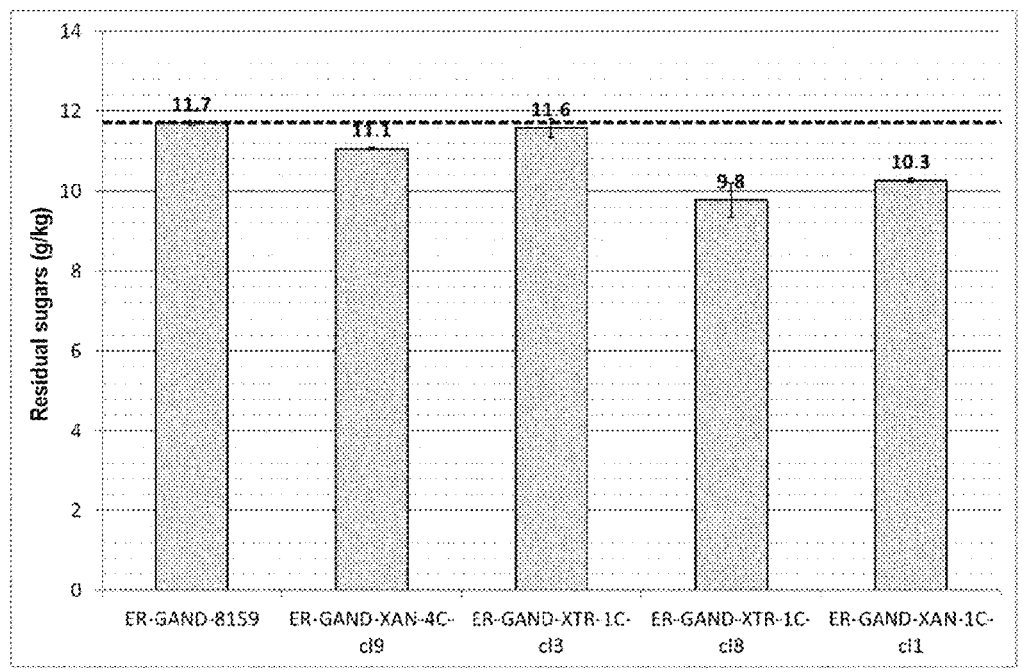
FIG. 3: Comparison of total sugars measured at the end of fermentation for the different strains studied.

Strains with a gain in ethanol production therefore have a parallel reduction in glycerol production. However, this reduction in glycerol does not explain the gain in alcohol production; the gain in yield comes from a more efficient consumption of the glucose in the medium made possible by the action of the xylanase produced by each strain. This result is confirmed by the measurements of total sugars at the end of fermentation presented in FIG. 3: strains with an advantage in ethanol yield also have a reduced residual sugar content.

TABLE 5

Results of Transformant Performance Tests

| | Absolute values (in %) Relative gains compared with the reference (%) | | | | |
|---|---|---|---|---|---|
| | Reference* | C11* | C19* | C13* | C18* |
| Percentage of glucose consumption (% w/w) | 95.9 | 96.4 (0.5) | 96.2 (0.2) | 96.0 (0.0) | 96.6 (0.7) |
| Ethanol content (g/kg) | 113.6 | 116.9 (2.8) | 117.0 (2.9) | 113.3 (−0.2) | 115.6 (1.7) |
| Volumetric productivity (g/kg/h) | 1.62 | 1.59 (−2.0) | 1.60 (−1.9) | 1.62 (−0.2) | 1.58 (−3.1) |
| Maximum volumetric productivity (g/kg/h) | 6.1 | 6.0 (−1.8) | 6.0 (−1.2) | 6.0 (−1.8) | 5.9 (−3.5) |
| Ethanol yield (% w/w) | 39.7 | 40.7 (2.5) | 40.7 (2.6) | 39.6 (−0.2) | 40.3 (1.7) |

TABLE 5-continued

Results of Transformant Performance Tests

| | Absolute values (in %) Relative gains compared with the reference (%) | | | | |
|---|---|---|---|---|---|
| | Reference* | Cl1* | Cl9* | Cl3* | Cl8* |
| Glycerol/ethanol ratio (% w/w) | 8.9 | 8.5 (−5.4) | 8.5 (−4.5) | 8.9 (0.1) | 8.3 (−7.6) |
| Glycerol yield (% w/w) | 3.43 | 3.31 (−3.6) | 3.35 (−2.2) | 3.42 (−0.2) | 3.20 (−7.1) |

*Reference = ER-GAND-8159;
Cl1 = ER-GAND-XAN-1C-cl1 (I-5201);
Cl9 = ER-GAND-XAN-4C-cl9 (I-5264);
Cl3 = ER-GAND-XTR-1C-cl3 (I-5265); and
Cl8 = ER-GAND-XTR-1C-cl8.

Conclusion. The introduction of genes encoding the *Aspergillus niger* xylanase in the ER-GAND-8159 strain (14997) significantly improved performance in ethanol production. The yield gain measured in fermentation on a corn hydrolysate was between 2.5% and 2.6% compared with the reference strain. The action of xylanase on the fermentation matrix is beneficial to the action of glucoamylases by allowing them better access to the starch in the medium while reducing the glycerol response of the strains. This dual gain in sugar (reduction of the flow directed towards glycerol and increase of the glucose released by the glucoamylases) leads to a better ethanol production. The ER-GAND-XTR-1c strain has a similar advantage, although slightly less in this example.

PCT (Original in electronic format)
(This sheet is not part of and does not count as a sheet of the international application)

| 0-1 | Form PCT/RO/134 Indications Relating to Deposited Microorganism(s) or Other Biological Material (PCT Rule 13bis) | |
|---|---|---|
| 0-1-1 | Prepared using | PCT Online Filing Version 3.51.000.263e MT/FOP 20141031/0.20.5.20 |
| 0-2 | International Application No. | |
| 0-3 | Applicant's or agent's file reference | BCT190246 QT |

| 1 | The indications made below relate to the deposited microorganism(s) or other biological material referred to in the description on: | |
|---|---|---|
| 1-1 | page | 24 |
| 1-2 | line | 5 |
| 1-3 | Identification of deposit | |
| 1-3-1 | Name of depositary institution | CNCM Collection nationale de cultures de micro-organismes (CNCM) |
| 1-3-2 | Address of depositary institution | Institut Pasteur, 25-28, Rue du Dr. Roux, 75724 Paris Cedex 15, France |
| 1-3-3 | Date of deposit | 20 December 2017 (20.12.2017) |
| 1-3-4 | Order number | CNCM I-5265 |
| 1-5 | Designated states for which indications are made | All the designations |
| 2 | The indications made below relate to the deposited microorganism(s) or other biological material referred to in the description on: | |
| 2-1 | page | 24 |
| 2-2 | line | 16 |
| 2-3 | Identification of deposit | |
| 2-3-1 | Name of depositary institution | CNCM Collection nationale de cultures de micro-organismes (CNCM) |

PCT (Original in electronic format)
(This sheet is not part of and does not count as a sheet of the international application)

| | | |
|---|---|---|
| 2-3-2 | Address of depositary institution | Institut Pasteur, 25-28, Rue du Dr. Roux, 75724 Paris Cedex 15, France |
| 2-3-3 | Date of deposit | 20 December 2017 (20.12.2017) |
| 2-3-4 | Order number | CNCM I-5264 |
| 2-5 | Designated states for which indications are made | All the designations |
| 3 | The indications made below relate to the deposited microorganism(s) or other biological material referred to in the description on: | |
| 3-1 | page | 4 |
| 3-2 | line | 25 |
| 3-3 | Identification of deposit | |
| 3-3-1 | Name of depositary institution | CNCM Collection nationale de cultures de micro-organismes (CNCM) |
| 3-3-2 | Address of depositary institution | Institut Pasteur, 25-28, Rue du Dr. Roux, 75724 Paris Cedex 15, France |
| 3-3-3 | Date of deposit | 26 April 2017 (26.04.2017) |
| 3-3-4 | Order number | CNCM I-5201 |
| 3-5 | Designated states for which indications are made | All the designations |
| 4 | The indications made below relate to the deposited microorganism(s) or other biological material referred to in the description on: | |
| 4-1 | page | 22 |
| 4-2 | line | 22 |
| 4-3 | Identification of deposit | |
| 4-3-1 | Name of depositary institution | CNCM Collection nationale de cultures de micro-organismes (CNCM) |
| 4-3-2 | Address of depositary institution | Institut Pasteur, 25-28, Rue du Dr. Roux, 75724 Paris Cedex 15, France |
| 4-3-3 | Date of deposit | 4 September 2008 (04.09.2008) |
| 4-3-4 | Order number | CNCM I-4071 |
| 4-5 | Designated states for which indications are made | All the designations |
| 5 | The indications made below relate to the deposited microorganism(s) or other biological material referred to in the description on: | |
| 5-1 | page | 13 |

PCT (Original in electronic format)
(This sheet is not part of and does not count as a sheet of the international application)

| 5-2 | line | 30 |
|---|---|---|
| 5-3 | Identification of deposit | |
| 5-3-1 | Name of depositary institution | CNCM Collection nationale de cultures de micro-organismes (CNCM) |
| 5-3-2 | Address of depositary institution | Institut Pasteur, 25-28, Rue du Dr. Roux, 75724 Paris Cedex 15, France |
| 5-3-3 | Date of deposit | 12 December 2013 (12.12.2013) |
| 5-3-4 | Order number | CNCM I-4829 |
| 5-5 | Designated states for which indications are made | All the designations |
| 6 | The indications made below relate to the deposited microorganism(s) or other biological material referred to in the description on: | |
| 6-1 | page | 5 |
| 6-2 | line | 7 |
| 6-3 | Identification of deposit | |
| 6-3-1 | Name of depositary institution | CNCM Collection nationale de cultures de micro-organismes (CNCM) |
| 6-3-2 | Address of depositary institution | Institut Pasteur, 25-28, Rue du Dr. Roux, 75724 Paris Cedex 15, France |
| 6-3-3 | Date of deposit | 9 July 2015 (09.07.2015) |
| 6-3-4 | Order number | CNCM I-4997 |
| 6-5 | Designated states for which indications are made | All the designations |
| 7 | The indications made below relate to the deposited microorganism(s) or other biological material referred to in the description on: | |
| 7-1 | page | 24 |
| 7-2 | line | 18 |
| 7-3 | Identification of deposit | |
| 7-3-1 | Name of depositary institution | CNCM Collection nationale de cultures de micro-organismes (CNCM) |
| 7-3-2 | Address of depositary institution | Institut Pasteur, 25-28, Rue du Dr. Roux, 75724 Paris Cedex 15, France |
| 7-3-3 | Date of deposit | 20 December 2017 (20.12.2017) |
| 7-3-4 | Order number | CNCM I-5266 |
| 7-5 | Designated states for which indications are made | All the designations |

PCT

(Original in electronic format)
(This sheet is not part of and does not count as a sheet of the international application)

FOR RECEIVING OFFICE USE ONLY

| 0-4 | This form was received with the international application:<br>(yes or no) | |
|---|---|---|
| 0-4-1 | Authorized officer | |

FOR INTERNATIONAL BUREAU USE ONLY

| 0-5 | This form was received by the international Bureau on: | |
|---|---|---|
| 0-5-1 | Authorized officer | |

The invention claimed is:

1. A *Saccharomyces cerevisiae* yeast strain, wherein said yeast strain co-expresses:
   a gene encoding a xylanase of *Aspergillus niger*, wherein the xylanase of *Aspergillus niger* is encoded by the nucleic acid sequence set forth in SEQ ID NO: 5;
   a gene encoding a glucoamylase of *Aspergillus niger*, wherein the glucoamylase of *Aspergillus niger* is encoded by the nucleic acid sequence set forth in SEQ ID NO: 1; and
   a gene encoding a glucoamylase of *Saccharomyces cerevisiae* var. *diastaticus*, wherein the glucoamylase of *Saccharomyces cerevisiae* var. *diastaticus* is encoded by the nucleic acid sequence set forth in SEQ ID NO: 3; and wherein said *Saccharomyces cerevisiae* yeast strain comprises:
      1 copy or 4 copies of the gene encoding a xylanase of *Aspergillus niger*;
      6 copies of the gene encoding a glucoamylase of *Aspergillus niger*; and
      4 copies of the gene encoding a glucoamylase of *Saccharomyces cerevisiae* var. *diastaticus*.

2. The *Saccharomyces cerevisiae* yeast strain according to claim 1, wherein the xylanase of *Aspergillus niger* consists of the polypeptide sequence SEQ ID NO: 6.

3. The *Saccharomyces cerevisiae* yeast strain according to claim 1, wherein the glucoamylase of *Saccharomyces cerevisiae* var. *diastaticus* consists of the polypeptide sequence SEQ ID NO: 4.

4. The *Saccharomyces cerevisiae* yeast strain according to claim 1, wherein the glucoamylase of *Aspergillus niger* consists of the polypeptide sequence SEQ ID NO: 2.

5. The *Saccharomyces cerevisiae* yeast strain according to claim 1, wherein the gene encoding the xylanase of *Aspergillus niger*, the gene encoding the glucoamylase of *Aspergillus niger*, and the gene encoding the glucoamylase of *Saccharomyces cerevisiae* var. *diastaticus* are integrated within the genome of said yeast strain.

6. The *Saccharomyces cerevisiae* yeast strain according to claim 1, wherein said yeast strain is the strain deposited on 26 Apr. 2017 in the CNCM under number I-5201.

7. A method for obtaining a *Saccharomyces cerevisiae* yeast strain useful for the production of bioethanol, said method comprising steps of:
   (a) genetically modifying a *Saccharomyces cerevisiae* yeast so that it co-expresses:
      a gene encoding a xylanase of *Aspergillus niger*, wherein the xylanase of *Aspergillus niger* is encoded by the nucleic acid sequence set forth in SEQ ID NO: 5, a gene encoding a glucoamylase of *Aspergillus niger*, wherein the glucoamylase of *Aspergillus niger* is encoded by the nucleic acid sequence set forth in SEQ ID NO: 1, and a gene encoding glucoamylase of *Saccharomyces cerevisiae* var. *diastaticus*, wherein the glucoamylase of *Saccharomyces cerevisiae* var. *diastaticus* is encoded by the nucleic acid sequence set forth in SEQ ID NO: 3 such that the genetically modified *Saccharomyces cerevisiae* yeast comprises:

1 copy or 4 copies of the gene encoding a xylanase of *Aspergillus niger*;

6 copies of the gene encoding a glucoamylase of *Aspergillus niger*; and 4 copies of the gene encoding a glucoamylase of *Saccharomyces cerevisiae* var. *diastaticus*, or obtaining a *Saccharomyces cerevisiae* yeast strain according to claim 1;

(b) culturing and fermenting the yeast obtained in step (a) on a synthetic dextrin medium; and (c) selecting at least one strain with fermentation kinetics at least equal to or greater than the fermentation kinetics of the strain deposited on 9 Jul. 2015 in the CNCM under number I-4997.

8. A method for increasing the bioethanol production yield of a *Saccharomyces cerevisiae* yeast strain, said method comprising steps of:

(a) providing a *Saccharomyces cerevisiae* yeast co-expressing a gene encoding a glucoamylase of *Aspergillus niger*, wherein the glucoamylase of *Aspergillus niger* is encoded by the nucleic acid sequence set forth in SEQ ID NO: 1, and a gene encoding glucoamylase of *Saccharomyces cerevisiae* var. *diastaticus* wherein the glucoamylase of *Saccharomyces cerevisiae* var. *diastaticus* is encoded by the nucleic acid sequence set forth in SEQ ID NO: 3;

(b) genetically modifying the yeast of step (a) so that it further expresses a gene encoding a xylanase of *Aspergillus niger*, wherein the xylanase of *Aspergillus niger* is encoded by the nucleic acid sequence set forth in SEQ ID NO: 5 such that the genetically modified *Saccharomyces cerevisiae* yeast comprises:

6 copies of the gene encoding a glucoamylase of *Aspergillus niger*;

4 copies of the gene encoding a glucoamylase of *Saccharomyces cerevisiae* var. *diastaticus*; and 1 copy or 4 copies of the gene encoding a xylanase of *Aspergillus niger*;

(c) culturing and fermenting the yeast obtained in step (b) on a synthetic dextrin medium; and (d) selecting at least one strain with fermentation kinetics at least equal to or greater than the fermentation kinetics of the strain deposited on 9 Jul. 2015 in the CNCM under number I-4997.

9. The method as claimed in claim 8, wherein the *Saccharomyces cerevisiae* yeast of step (a) is the *Saccharomyces cerevisiae* yeast strain deposited on 9 Jul. 2015 in the CNCM under number I-4997.

10. A method for producing bioethanol from biomass, said method comprising steps of:

(a) pre-hydrolyzing and liquefying the starch from the biomass;

(b) reacting the liquefied starch obtained in step (a) with a *Saccharomyces cerevisiae* yeast strain according to claim 1 to produce bioethanol; and (c) extracting the bioethanol produced in step (b).

* * * * *

SEQUENCE LISTING

<160> NUMBER OF SEQ ID NOS: 20

<210> SEQ ID NO 1
<211> LENGTH: 1923
<212> TYPE: DNA
<213> ORGANISM: Aspergillus niger

<400> SEQUENCE: 1

```
atgtccttta gatcattgct tgcactgtct ggtttagttt gcactggact tgccaatgtc      60
atctctaaga gagcgacact agattcctgg ttaagtaacg aagccactgt tgcacgtaca     120
gccatactta acaacatagg tgccgatgga gcatgggtta gtggcgcaga ttcggggata     180
gtcgttgcca gtccatcgac tgataatcct gactactttt atacctgac ccgtgatagt      240
gggttggtgc tgaaaacatt ggtagacctt ttcagaaacg gtgatacgtc cttgctatca     300
accatagaga attacattag cgcacaagct attgtacaag gcatttccaa tccgagtggc     360
gatctaagtt caggcgctgg cttgggtgaa cccaagttca atgtcgatga aactgcatat     420
acgggatcat ggggtagacc acaaagagat ggtccagctc taagagcaac tgccatgatt     480
ggatttggcc aatggctttt ggataatggc tacactagta cagccacaga cattgtttgg     540
cctttagtca gaaatgacct atcttatgtg gctcaatatt ggaaccaaac aggttatgac     600
ttatgggaag aagtcaatgg ttcttctttc tttacaattg ccgtacagca tcgtgcactg     660
gtggaaggat cggctttcgc cactgccgta ggttcctcat gtagttggtg tgattcacaa     720
gcgccagaga ttctatgcta tttgcagagc ttctggacag ggagttttat cttagccaac     780
ttcgatagct ctagatccgg gaaagatgct aatacccctat aggctcaat acacacgttt     840
gacccctgaag ctgcttgtga cgattctaca tttcaaccgt gttctcccag gctttggca    900
aaccataaag aagttgttga ctcttttagg tctatctaca ccttaaacga cggtttgtcg     960
gattcagaag ctgtggcagt tgggaggtat ccggaggata cgtactacaa tggtaatcct    1020
tggttccttt gcactttggc agccgcggag cagttatatg atgcgttata tcaatgggat    1080
aagcagggtt cctagaggt aactgatgtg tcgctggact tctttaaagc gctgtattca    1140
gatgctgcta ccggtacgta ttcttcgtca tcttcaacct attccagcat tgtggatgct    1200
gtcaagactt ttgcagacgg atttgtcagt atagttgaga ctcatgcagc ttctaatggt    1260
tctatgtccg aacagtacga caaaagcgat ggtgaacaat tgtcagcaag agacttgacc    1320
tggtcttatg cagccttgtt aacagccaac aataggagaa atagcgttgt tccagctagt    1380
tgggagaaa catccgcgtc atcagttcca ggaacgtgtg ctgctacttc agctattggt    1440
acatattctt cagttacagt cacctcttgg ccttcgatag tagctactgg aggaactact    1500
acgaccgcta ctcctacagg tagcggttct gtgacttcca cctcaaagac aactgctact    1560
gctagcaaaa catctacctc tacttcgtcc acatcatgca ctaccccaac tgcagtcgca    1620
gttacgtttg atttgacagc tactacaacg tacggggaaa acatttactt ggtaggtagc    1680
atcagtcaat tgggcgactg ggaaaccagc gatggtattg cattgagtgc agataaatac    1740
acttcctctg atccattatg gtatgttacc gttacgttac cagctggtga gtcctttgaa    1800
tacaagttca tcagaatcga gagtgatgac tctgtggaat gggaatctga tcccaataga    1860
gaatacacag tacctcaagc gtgtggtaca tcaacagcca ccgtaactga tacttggagg    1920
taa                                                                    1923
```

<210> SEQ ID NO 2
<211> LENGTH: 640

<212> TYPE: PRT
<213> ORGANISM: Aspergillus niger

<400> SEQUENCE: 2

```
Met Ser Phe Arg Ser Leu Leu Ala Leu Ser Gly Leu Val Cys Thr Gly
1               5                   10                  15

Leu Ala Asn Val Ile Ser Lys Arg Ala Thr Leu Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Glu Val Asn Gly Ser
        195                 200                 205

Ser Phe Phe Thr Ile Ala Val Gln His Arg Ala Leu Val Glu Gly Ser
    210                 215                 220

Ala Phe Ala Thr Ala Val Gly Ser Ser Cys Ser Trp Cys Asp Ser Gln
225                 230                 235                 240

Ala Pro Glu Ile Leu Cys Tyr Leu Gln Ser Phe Trp Thr Gly Ser Phe
                245                 250                 255

Ile Leu Ala Asn Phe Asp Ser Ser Arg Ser Gly Lys Asp Ala Asn Thr
            260                 265                 270

Leu Leu Gly Ser Ile His Thr Phe Asp Pro Glu Ala Ala Cys Asp Asp
        275                 280                 285

Ser Thr Phe Gln Pro Cys Ser Pro Arg Ala Leu Ala Asn His Lys Glu
    290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Ala Glu Gln Leu
            340                 345                 350

Tyr Asp Ala Leu Tyr Gln Trp Asp Lys Gln Gly Ser Leu Glu Val Thr
        355                 360                 365

Asp Val Ser Leu Asp Phe Phe Lys Ala Leu Tyr Ser Asp Ala Ala Thr
    370                 375                 380

Gly Thr Tyr Ser Ser Ser Ser Ser Thr Tyr Ser Ser Ile Val Asp Ala
385                 390                 395                 400
```

Val Lys Thr Phe Ala Asp Gly Phe Val Ser Ile Val Glu Thr His Ala
            405                 410                 415

Ala Ser Asn Gly Ser Met Ser Glu Gln Tyr Asp Lys Ser Asp Gly Glu
        420                 425                 430

Gln Leu Ser Ala Arg Asp Leu Thr Trp Ser Tyr Ala Ala Leu Leu Thr
            435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Ser Thr
            515                 520                 525

Ser Ser Thr Ser Cys Thr Thr Pro Thr Ala Val Ala Val Thr Phe Asp
    530                 535                 540

Leu Thr Ala Thr Thr Thr Tyr Gly Glu Asn Ile Tyr Leu Val Gly Ser
545                 550                 555                 560

Ile Ser Gln Leu Gly Asp Trp Glu Thr Ser Asp Gly Ile Ala Leu Ser
                565                 570                 575

Ala Asp Lys Tyr Thr Ser Ser Asp Pro Leu Trp Tyr Val Thr Val Thr
            580                 585                 590

Leu Pro Ala Gly Glu Ser Phe Glu Tyr Lys Phe Ile Arg Ile Glu Ser
            595                 600                 605

Asp Asp Ser Val Glu Trp Glu Ser Asp Pro Asn Arg Glu Tyr Thr Val
    610                 615                 620

Pro Gln Ala Cys Gly Thr Ser Thr Ala Thr Val Thr Asp Thr Trp Arg
625                 630                 635                 640

<210> SEQ ID NO 3
<211> LENGTH: 2418
<212> TYPE: DNA
<213> ORGANISM: Saccharomyces cerevisiae var. diastaticus

<400> SEQUENCE: 3

| | | |
|---|---|---|
| atgcaaagac catttctact cgcttatttg gtcctttcgc ttctatttaa ctcagctttg | 60 |
| ggttttccaa ctgcactagt tcctagagga tcctcctcta gcaacatcac ttcctccggt | 120 |
| ccatcttcaa ctccattcag ctctgctact gaaagctttt ctactggcac tactgtcact | 180 |
| ccatcatcat ccaaataccc tggcagtaaa acagaaactt ctgtttcttc tacaaccgaa | 240 |
| actaccattg ttccaactac aactacgact tctgtcataa caccatcaac aaccactatt | 300 |
| accactacgg tttgctctac aggaacaaac tctgccggtg aaactacttc tggatgctct | 360 |
| ccaaagacca ttacaactac tgttccatgt tcaaccagtc aagcgaaaac cgcatcggaa | 420 |
| tcaacaacca cttcacctac cacacctgta actacagttg tctcaaccac cgtcgttact | 480 |
| actgagtatt ctactagtac aaaacaaggt ggtgaaatta aactacatt tgtcaccaaa | 540 |
| aacattccaa ccacttacct aactacaatt gctccaactt catcagtcac tacggttacc | 600 |
| aatttcaccc caaccactat tactactacg gtttgctcta caggaacaaa ctctgccggt | 660 |
| gaaactacct ctggatgctc tccaaagact gtcacaacaa ctgttccttg ttcaactggt | 720 |
| actggcgaat acactactga agctaccgcc cctgttacaa cagctgtcac aaccaccgtt | 780 |

-continued

```
gttaccactg aatcctctac gggtactaac tccgctggta agacgacaac tagttacaca    840
acaaagtctg taccaaccac ctatgtattt gactttggca agggcattct cgatcaaagc    900
tgcggcggtg tattttcaaa caacggctct tcgcaagtgc agctgcggga tgtagtcttg    960
atgaatggga cagtggtata cgattcaaac ggcgcttggg acagtagtcc gctggaggag   1020
tggctccagc gacagaaaaa agtttccatc gaaagaatat ttgaaaatat tgggcccagc   1080
gccgtgtatc cgtctatttt gcctggggtc gtgattgcgt caccatcgca aacgcatcca   1140
gactacttct accaatggat aagggacagc gcgttgacga taaacagtat tgtctctcat   1200
tctgcggacc cggcaataga gacgttattg cagtacctga acgtttcatt ccacttgcaa   1260
agaaccaaca acacattggg cgctggcatt ggttacacta cgatacagt ggctttggga    1320
gaccctaagt ggaacgtcga caacacggct tcacggaaac cttggggtcg tcctcaaaac   1380
gatggccctg ctcttcgaag cattgccatc ttaaaaatca tcgactacat caagcaatct   1440
ggcactgatc tgggggccaa gtacccattc cagtccaccg cagatatctt tgatgatatt   1500
gtacgttggg acctgaggtt cattattgac cactggaatt cttccggatt tgatctatgg   1560
gaggaagtca atggcatgca tttctttact ttactggtac aactgtctgc agtggacagg   1620
tcgctgtcgt attttaacgc tcagaacgg tcgtctccct tgttgaaga attgcgtcag     1680
acacgccggg acatctccaa gttttagtg gaccctgcga tgggtttat caacggcaag    1740
tacaattata ttgttgagac acccatgatt gccgacacat tgagatccgg actggacata   1800
tccactttat tagctgcgaa caccgtccac gatgcgccat ctgcttccca tcttccgttc   1860
gatatcaatg accctgccgt cctgaacacg ttgcaccatt tgatgttgca catgcgttcg   1920
atataccca tcaacgatag ctccaaaaat gcaacgggta ttgccctggg ccggtatcct    1980
gaggacgtat atgatggata tggcgttggc gagggaaatc cctgggtcct ggccacgtgt   2040
gccgcttcaa caacgcttta tcagctcatt tacagacaca tctctgagca gcatgacttg   2100
gttgtcccaa tgaacaacga ttgttcgaac gcattttgga gcgagctggt attctccaac   2160
ctcacgactt tgggaaatga cgaaggctat ttgattttgg agttcaatac acctgccttc   2220
aatcaaacca tacaaaaaat cttccaacta gctgattcat ttcttggtca agctgaaagc   2280
cacgtgggaa cagacgggga actaagtgaa caatttaaca aatacacagg gtttatgcag   2340
ggtgcccaac accttacctg gtcctatact tcattctggg atgcctatca aataagacaa   2400
gaagttttac agagtttg                                                 2418
```

<210> SEQ ID NO 4
<211> LENGTH: 806
<212> TYPE: PRT
<213> ORGANISM: Saccharomyces cerevisiae var. diastaticus

<400> SEQUENCE: 4

```
Met Gln Arg Pro Phe Leu Leu Ala Tyr Leu Val Leu Ser Leu Leu Phe
1               5                   10                  15

Asn Ser Ala Leu Gly Phe Pro Thr Ala Leu Val Pro Arg Gly Ser Ser
            20                  25                  30

Ser Ser Asn Ile Thr Ser Ser Gly Pro Ser Ser Thr Pro Phe Ser Ser
        35                  40                  45

Ala Thr Glu Ser Phe Ser Thr Gly Thr Thr Val Thr Pro Ser Ser Ser
    50                  55                  60

Lys Tyr Pro Gly Ser Lys Thr Glu Thr Ser Val Ser Ser Thr Thr Glu
65                  70                  75                  80
```

-continued

```
Thr Thr Ile Val Pro Thr Thr Thr Thr Ser Val Ile Thr Pro Ser
             85                  90                  95

Thr Thr Thr Ile Thr Thr Thr Val Cys Ser Thr Gly Thr Asn Ser Ala
            100                 105                 110

Gly Glu Thr Thr Ser Gly Cys Ser Pro Lys Thr Ile Thr Thr Thr Val
            115                 120                 125

Pro Cys Ser Thr Ser Pro Ser Glu Thr Ala Ser Glu Ser Thr Thr Thr
    130                 135                 140

Ser Pro Thr Thr Pro Val Thr Val Val Ser Thr Thr Val Val Thr
145                 150                 155                 160

Thr Glu Tyr Ser Thr Ser Thr Lys Gln Gly Gly Glu Ile Thr Thr Thr
                165                 170                 175

Phe Val Thr Lys Asn Ile Pro Thr Thr Tyr Leu Thr Thr Ile Ala Pro
            180                 185                 190

Thr Ser Ser Val Thr Thr Val Thr Asn Phe Thr Pro Thr Thr Ile Thr
            195                 200                 205

Thr Thr Val Cys Ser Thr Gly Thr Asn Ser Ala Gly Glu Thr Thr Ser
    210                 215                 220

Gly Cys Ser Pro Lys Thr Val Thr Thr Val Pro Cys Ser Thr Gly
225                 230                 235                 240

Thr Gly Glu Tyr Thr Thr Glu Ala Thr Ala Pro Val Thr Thr Ala Val
                245                 250                 255

Thr Thr Thr Val Val Thr Thr Glu Ser Ser Thr Gly Thr Asn Ser Ala
            260                 265                 270

Gly Lys Thr Thr Thr Ser Tyr Thr Thr Lys Ser Val Pro Thr Thr Tyr
            275                 280                 285

Val Phe Asp Phe Gly Lys Gly Ile Leu Asp Gln Ser Cys Gly Gly Val
    290                 295                 300

Phe Ser Asn Asn Gly Ser Ser Gln Val Gln Leu Arg Asp Val Val Leu
305                 310                 315                 320

Met Asn Gly Thr Val Val Tyr Asp Ser Asn Gly Ala Trp Asp Ser Ser
                325                 330                 335

Pro Leu Glu Glu Trp Leu Gln Arg Gln Lys Lys Val Ser Ile Glu Arg
            340                 345                 350

Ile Phe Glu Asn Ile Gly Pro Ser Ala Val Tyr Pro Ser Ile Leu Pro
            355                 360                 365

Gly Val Val Ile Ala Ser Pro Ser Gln Thr His Pro Asp Tyr Phe Tyr
    370                 375                 380

Gln Trp Ile Arg Asp Ser Ala Leu Thr Ile Asn Ser Ile Val Ser His
385                 390                 395                 400

Ser Ala Asp Pro Ala Ile Glu Thr Leu Leu Gln Tyr Leu Asn Val Ser
                405                 410                 415

Phe His Leu Gln Arg Thr Asn Asn Thr Leu Gly Ala Gly Ile Gly Tyr
            420                 425                 430

Thr Asn Asp Thr Val Ala Leu Gly Asp Pro Lys Trp Asn Val Asp Asn
            435                 440                 445

Thr Ala Phe Thr Glu Pro Trp Gly Arg Pro Gln Asn Asp Gly Pro Ala
    450                 455                 460

Leu Arg Ser Ile Ala Ile Leu Lys Ile Ile Asp Tyr Ile Lys Gln Ser
465                 470                 475                 480

Gly Thr Asp Leu Gly Ala Lys Tyr Pro Phe Gln Ser Thr Ala Asp Ile
                485                 490                 495
```

```
Phe Asp Asp Ile Val Arg Trp Asp Leu Arg Phe Ile Ile Asp His Trp
            500                 505                 510
Asn Ser Ser Gly Phe Asp Leu Trp Glu Glu Val Asn Gly Met His Phe
        515                 520                 525
Phe Thr Leu Leu Val Gln Leu Ser Ala Val Asp Arg Ser Leu Ser Tyr
    530                 535                 540
Phe Asn Ala Ser Glu Arg Ser Ser Pro Phe Val Glu Glu Leu Arg Gln
545                 550                 555                 560
Thr Arg Arg Asp Ile Ser Lys Phe Leu Val Asp Pro Ala Asn Gly Phe
                565                 570                 575
Ile Asn Gly Lys Tyr Asn Tyr Ile Val Glu Thr Pro Met Ile Ala Asp
            580                 585                 590
Thr Leu Arg Ser Gly Leu Asp Ile Ser Thr Leu Leu Ala Ala Asn Thr
        595                 600                 605
Val His Asp Ala Pro Ser Ala Ser His Leu Pro Phe Asp Ile Asn Asp
    610                 615                 620
Pro Ala Val Leu Asn Thr Leu His His Leu Met Leu His Met Arg Ser
625                 630                 635                 640
Ile Tyr Pro Ile Asn Asp Ser Ser Lys Asn Ala Thr Gly Ile Ala Leu
                645                 650                 655
Gly Arg Tyr Pro Glu Asp Val Tyr Asp Gly Tyr Gly Val Gly Glu Gly
            660                 665                 670
Asn Pro Trp Val Leu Ala Thr Cys Ala Ala Ser Thr Thr Leu Tyr Gln
        675                 680                 685
Leu Ile Tyr Arg His Ile Ser Glu Gln His Asp Leu Val Val Pro Met
    690                 695                 700
Asn Asn Asp Cys Ser Asn Ala Phe Trp Ser Glu Leu Val Phe Ser Asn
705                 710                 715                 720
Leu Thr Thr Leu Gly Asn Asp Glu Gly Tyr Leu Ile Leu Glu Phe Asn
                725                 730                 735
Thr Pro Ala Phe Asn Gln Thr Ile Gln Lys Ile Phe Gln Leu Ala Asp
            740                 745                 750
Ser Phe Leu Gly Gln Ala Glu Ser His Val Gly Thr Asp Gly Glu Leu
        755                 760                 765
Ser Glu Gln Phe Asn Lys Tyr Thr Gly Phe Met Gln Gly Ala Gln His
    770                 775                 780
Leu Thr Trp Ser Tyr Thr Ser Phe Trp Asp Ala Tyr Gln Ile Arg Gln
785                 790                 795                 800
Glu Val Leu Gln Ser Leu
                805

<210> SEQ ID NO 5
<211> LENGTH: 636
<212> TYPE: DNA
<213> ORGANISM: Artificial Sequence
<220> FEATURE:
<223> OTHER INFORMATION: Siquence consensus du ghne XYN1 qui code pour
      la xylanase d'Aspergillus niger

<400> SEQUENCE: 5
atgaaggtca ctgcggcttt tgcaggtctt ttggtcacgg cattcgccgc tcctgtgccg       60
gaacctgttc tggtgtcgcg aagtgctggt attaactacg tgcaaaacta caacggcaac      120
cttggtgatt tcacctatga cgagagtgcc ggaacatttt ccatgtactg gaagatgga       180 gtgagctccg actttgtcgt tggtctgggc tggaccactg gttcttctaa cgctatcacc      240
```

```
tactctgccg aatacagcgc ttctggctcc tcttcctacc tcgctgtgta cggctgggtc      300
aactatcctc aggctgaata ctacatcgtc gaggattacg gtgattacaa cccttgcagc      360
tcggccacaa gccttggtac cgtgtactct gatggaagca cctaccaagt ctgcaccgac      420
actcgaacta cgaaccgtc catcacggga acaagcacgt tcacgcagta cttctccgtt      480
cgagagagca cgcgcacatc tggaacggtg actgttgcca accatttcaa cttctgggcg      540
cagcatgggt tcggaaatag cgacttcaat tatcaggtca tggcagtgga agcatggagc      600
ggtgctggca gcgccagtgt cacgatctcc tcttaa                               636
```

<210> SEQ ID NO 6
<211> LENGTH: 211
<212> TYPE: PRT
<213> ORGANISM: Aspergillus niger

<400> SEQUENCE: 6

```
Met Lys Val Thr Ala Ala Phe Ala Gly Leu Leu Val Thr Ala Phe Ala
1               5                   10                  15

Ala Pro Val Pro Glu Pro Val Leu Val Ser Arg Ser Ala Gly Ile Asn
                20                  25                  30

Tyr Val Gln Asn Tyr Asn Gly Asn Leu Gly Asp Phe Thr Tyr Asp Glu
            35                  40                  45

Ser Ala Gly Thr Phe Ser Met Tyr Trp Glu Asp Gly Val Ser Ser Asp
        50                  55                  60

Phe Val Val Gly Leu Gly Trp Thr Thr Gly Ser Ser Asn Ala Ile Thr
65                  70                  75                  80

Tyr Ser Ala Glu Tyr Ser Ala Ser Gly Ser Ser Ser Tyr Leu Ala Val
                85                  90                  95

Tyr Gly Trp Val Asn Tyr Pro Gln Ala Glu Tyr Tyr Ile Val Glu Asp
            100                 105                 110

Tyr Gly Asp Tyr Asn Pro Cys Ser Ser Ala Thr Ser Leu Gly Thr Val
        115                 120                 125

Tyr Ser Asp Gly Ser Thr Tyr Gln Val Cys Thr Asp Thr Arg Thr Asn
    130                 135                 140

Glu Pro Ser Ile Thr Gly Thr Ser Thr Phe Thr Gln Tyr Phe Ser Val
145                 150                 155                 160

Arg Glu Ser Thr Arg Thr Ser Gly Thr Val Thr Val Ala Asn His Phe
                165                 170                 175

Asn Phe Trp Ala Gln His Gly Phe Gly Asn Ser Asp Phe Asn Tyr Gln
            180                 185                 190

Val Met Ala Val Glu Ala Trp Ser Gly Ala Gly Ser Ala Ser Val Thr
        195                 200                 205

Ile Ser Ser
    210
```

<210> SEQ ID NO 7
<211> LENGTH: 672
<212> TYPE: DNA
<213> ORGANISM: Artificial Sequence
<220> FEATURE:
<223> OTHER INFORMATION: Siquence consensus du ghne XYN2 sans intron,
      qui code pour la xylanase de Trichoderma reesei

<400> SEQUENCE: 7

```
atggtttctt tcacttcttt gttggctggt gttgctgcta tctctggtgt tttggctgct       60
ccagctgctg aagttgaatc tgttgctgtt gaaaagagac agacgattca gcccggcacg      120
```

```
ggctacaaca acggctactt ctactcgtac tggaacgatg gccacggcgg cgtgacgtac    180
accaatggtc ccggcgggca gttctccgtc aactggtcca actcgggcaa ctttgtcggc    240
ggcaagggat ggcagcccgg caccaagaac aaggtcatca acttctcggg cagctacaac    300
cccaacggca cagctacct ctccgtgtac ggctggtccc gcaaccccct gatcgagtac    360
tacatcgtcg agaactttgg cacctacaac ccgtccacgg cgccaccaa gctgggcgag    420 gtcacctccg acggcagcgt ctacgacatt taccgcacgc agcgcgtcaa ccagccgtcc    480
atcatcggca ccgccacctt ttaccagtac tggtccgtcc gccgcaacca ccgctcgagc    540
ggctccgtca acacggcgaa ccacttcaac gcgtgggctc agcaaggcct gacgctcggg    600
acgatggatt accagattgt tgccgtggag ggttactta gctctggctc tgcttccatc    660
accgtcagct aa                                                        672
```

<210> SEQ ID NO 8
<211> LENGTH: 223
<212> TYPE: PRT
<213> ORGANISM: Artificial Sequence
<220> FEATURE:
<223> OTHER INFORMATION: Siquence protiique de la xylanase de Trichoderma reesei

<400> SEQUENCE: 8

```
Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
            20                  25                  30

Arg Gln Thr Ile Gln Pro Gly Thr Gly Tyr Asn Asn Gly Tyr Phe Tyr
        35                  40                  45

Ser Tyr Trp Asn Asp Gly His Gly Gly Val Thr Tyr Thr Asn Gly Pro
    50                  55                  60

Gly Gly Gln Phe Ser Val Asn Trp Ser Asn Ser Gly Asn Phe Val Gly
65                  70                  75                  80

Gly Lys Gly Trp Gln Pro Gly Thr Lys Asn Lys Val Ile Asn Phe Ser
                85                  90                  95

Gly Ser Tyr Asn Pro Asn Gly Asn Ser Tyr Leu Ser Val Tyr Gly Trp
            100                 105                 110

Ser Arg Asn Pro Leu Ile Glu Tyr Tyr Ile Val Glu Asn Phe Gly Thr
        115                 120                 125

Tyr Asn Pro Ser Thr Gly Ala Thr Lys Leu Gly Glu Val Thr Ser Asp
    130                 135                 140

Gly Ser Val Tyr Asp Ile Tyr Arg Thr Gln Arg Val Asn Gln Pro Ser
145                 150                 155                 160

Ile Ile Gly Thr Ala Thr Phe Tyr Gln Tyr Trp Ser Val Arg Arg Asn
                165                 170                 175

His Arg Ser Ser Gly Ser Val Asn Thr Ala Asn His Phe Asn Ala Trp
            180                 185                 190

Ala Gln Gln Gly Leu Thr Leu Gly Thr Met Asp Tyr Gln Ile Val Ala
        195                 200                 205

Val Glu Gly Tyr Phe Ser Ser Gly Ser Ala Ser Ile Thr Val Ser
    210                 215                 220
```

<210> SEQ ID NO 9
<211> LENGTH: 1545
<212> TYPE: DNA
<213> ORGANISM: Saccharomycopsis fibuligera

<400> SEQUENCE: 9

```
atgatcagat tgaccgtttt cttgaccgct gttttgctg ctgttgcttc ttgtgttcca      60
gttgaattgg ataagagaaa caccggtcat ttccaagctt attctggtta taccgttgct    120
agatctaact tcacccaatg gattcatgaa caaccagctg tttcttggta ctacttgttg    180
caaaacatcg attacccaga aggtcaattc aaatctgcta accaggtgt tgttgttgct     240
tctccatcta catctgaacc agattacttc taccaatgga ctagagatac cgctattacc    300
ttcttgtcct tgattgctga agttgaagat cattctttct ccaacactac cttggctaag    360
gttgtcgaat attacatttc caacacctac accttgcaaa gagtttctaa tccatccggt    420
aacttcgatt ctccaaatca tgatggtttg ggtgaaccta agttcaacgt tgatgatact    480
gcttatacag cttcttgggg tagaccacaa aatgatggtc cagctttgag agcttacgct    540
atttctagat acttgaacgc tgttgctaag cacaacaacg gtaaattatt attggccggt    600
caaaacggta ttccttattc ttctgcttcc gatatctact ggaagattat taagccagac    660
ttgcaacatg tttctactca ttggtctacc tctggttttg atttgtggga agaaaatcaa    720
ggtactcatt tcttcaccgc tttggttcaa ttgaaggctt tgtcttacgg tattccattg    780
tctaagacct acaatgatcc aggtttcact tcttggttgg aaaaacaaaa ggatgccttg    840
aactcctaca ttaactcttc cggtttcgtt aactctggta aaagcacat cgttgaatct    900
ccacaattgt catctagagg tggtttggat tctgctactt atattgctgc cttgatcacc    960
catgatatcg gtgatgatga tacttacacc ccattcaatg ttgataactc ctacgttttg   1020
aactccttgt attacctatt ggtcgacaac aagaacagat acaagatcaa cggtaactac   1080
aaagctggtg ctgctgttgg tagatatcct gaagatgttt acaacggtgt tggtacttct   1140
gaaggtaatc catggcaatt ggctactgct tatgctggtc aaactttta caccttggcc    1200
tacaattcct tgaagaacaa gaagaacttg gtcatcgaaa agttgaacta cgacttgtac   1260
aactccttca ttgctgattt gtccaagatt gattcttcct acgcttctaa ggattctttg   1320
actttgacct acggttccga taactacaag aacgttatca gtccttgtt gcaattcggt    1380
gactcattct tgaaggtttt gttggatcac atcgatgaca acggtcaatt gactgaagaa   1440
atcaacagat acaccggttt tcaagctggt gcagtttctt tgacttggtc atctggttct   1500
ttgttgtctg ctaatagagc cagaaacaag ttgatcgaat tattg                   1545
```

<210> SEQ ID NO 10
<211> LENGTH: 515
<212> TYPE: PRT
<213> ORGANISM: Saccharomycopsis fibuligera

<400> SEQUENCE: 10

```
Met Ile Arg Leu Thr Val Phe Leu Thr Ala Val Phe Ala Ala Val Ala
1               5                   10                  15

Ser Cys Val Pro Val Glu Leu Asp Lys Arg Asn Thr Gly His Phe Gln
            20                  25                  30

Ala Tyr Ser Gly Tyr Thr Val Ala Arg Ser Asn Phe Thr Gln Trp Ile
        35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95
```

```
Thr Ala Ile Thr Phe Leu Ser Leu Ile Ala Glu Val Glu Asp His Ser
            100                 105                 110

Phe Ser Asn Thr Thr Leu Ala Lys Val Val Glu Tyr Tyr Ile Ser Asn
            115                 120                 125

Thr Tyr Thr Leu Gln Arg Val Ser Asn Pro Ser Gly Asn Phe Asp Ser
        130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
                180                 185                 190

Asn Gly Lys Leu Leu Leu Ala Gly Gln Asn Gly Ile Pro Tyr Ser Ser
            195                 200                 205

Ala Ser Asp Ile Tyr Trp Lys Ile Lys Pro Asp Leu Gln His Val
            210                 215                 220

Ser Thr His Trp Ser Thr Ser Gly Phe Asp Leu Trp Glu Glu Asn Gln
225                 230                 235                 240

Gly Thr His Phe Phe Thr Ala Leu Val Gln Leu Lys Ala Leu Ser Tyr
                245                 250                 255

Gly Ile Pro Leu Ser Lys Thr Tyr Asn Asp Pro Gly Phe Thr Ser Trp
            260                 265                 270

Leu Glu Lys Gln Lys Asp Ala Leu Asn Ser Tyr Ile Asn Ser Ser Gly
        275                 280                 285

Phe Val Asn Ser Gly Lys Lys His Ile Val Glu Ser Pro Gln Leu Ser
        290                 295                 300

Ser Arg Gly Gly Leu Asp Ser Ala Thr Tyr Ile Ala Ala Leu Ile Thr
305                 310                 315                 320

His Asp Ile Gly Asp Asp Asp Thr Tyr Thr Pro Phe Asn Val Asp Asn
                325                 330                 335

Ser Tyr Val Leu Asn Ser Leu Tyr Tyr Leu Val Asp Asn Lys Asn
            340                 345                 350

Arg Tyr Lys Ile Asn Gly Asn Tyr Lys Ala Gly Ala Ala Val Gly Arg
        355                 360                 365

Tyr Pro Glu Asp Val Tyr Asn Gly Val Gly Thr Ser Glu Gly Asn Pro
    370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Asn Leu Val Ile Glu Lys Leu Asn
                405                 410                 415

Tyr Asp Leu Tyr Asn Ser Phe Ile Ala Asp Leu Ser Lys Ile Asp Ser
            420                 425                 430

Ser Tyr Ala Ser Lys Asp Ser Leu Thr Leu Thr Tyr Gly Ser Asp Asn
        435                 440                 445

Tyr Lys Asn Val Ile Lys Ser Leu Leu Gln Phe Gly Asp Ser Phe Leu
    450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510
```

Glu Leu Leu
      515

<210> SEQ ID NO 11
<211> LENGTH: 70
<212> TYPE: DNA
<213> ORGANISM: Artificial Sequence
<220> FEATURE:
<223> OTHER INFORMATION: amorce sens MCI-pADH1-BUD5-F

<400> SEQUENCE: 11
cgctccagaa ttagcggacc tcttgagcgg tgagcctctg gcaaagaaga gcataaccgc    60
tagagtactt                                                          70

<210> SEQ ID NO 12
<211> LENGTH: 52
<212> TYPE: DNA
<213> ORGANISM: Artificial Sequence
<220> FEATURE:
<223> OTHER INFORMATION: amorce anti-sens A1-Gibson AMG

<400> SEQUENCE: 12
tcactgtacg gtgagaacgt agatggtgtg cgcataggcc actagtggat ct            52

<210> SEQ ID NO 13
<211> LENGTH: 50
<212> TYPE: DNA
<213> ORGANISM: Artificial Sequence
<220> FEATURE:
<223> OTHER INFORMATION: amorce sens A2-Gibson AMG

<400> SEQUENCE: 13
cacaccatct acgttctcac cgtacagtga gcataaccgc tagagtactt               50

<210> SEQ ID NO 14
<211> LENGTH: 70
<212> TYPE: DNA
<213> ORGANISM: Artificial Sequence
<220> FEATURE:
<223> OTHER INFORMATION: amorce anti-sens MCI-tCYC1-BUD5-r

<400> SEQUENCE: 14
ctcaagaacg taggacgata actggttgga aagcgtaaac acggagtcaa cagcttgcaa    60
attaaagcct                                                          70

<210> SEQ ID NO 15
<211> LENGTH: 50
<212> TYPE: DNA
<213> ORGANISM: Artificial Sequence
<220> FEATURE:
<223> OTHER INFORMATION: amorce anti-sens B1-Gibson AMG

<400> SEQUENCE: 15
ttacgtagac tgagtagcaa cggttgagga cagcttgcaa attaaagcct               50

<210> SEQ ID NO 16
<211> LENGTH: 50
<212> TYPE: DNA
<213> ORGANISM: Artificial Sequence
<220> FEATURE:
<223> OTHER INFORMATION: amorce sens B2-Gibson AMG

<400> SEQUENCE: 16
tcctcaaccg ttgctactca gtctacgtaa gcataaccgc tagagtactt               50

```
<210> SEQ ID NO 17
<211> LENGTH: 50
<212> TYPE: DNA
<213> ORGANISM: Artificial Sequence
<220> FEATURE:
<223> OTHER INFORMATION: amorce anti-sens C1-Gibson AMG

<400> SEQUENCE: 17
tcagtagcac agagaagtgt aggagtgtag cagcttgcaa attaaagcct              50

<210> SEQ ID NO 18
<211> LENGTH: 50
<212> TYPE: DNA
<213> ORGANISM: Artificial Sequence
<220> FEATURE:
<223> OTHER INFORMATION: amorce sens C2-Gibson AMG

<400> SEQUENCE: 18
ctacactcct acacttctct gtgctactga gcataaccgc tagagtactt              50

<210> SEQ ID NO 19
<211> LENGTH: 50
<212> TYPE: DNA
<213> ORGANISM: Artificial Sequence
<220> FEATURE:
<223> OTHER INFORMATION: amorce anti-sens D1-Gibson AMG

<400> SEQUENCE: 19
ttaggataca tgcagtagac gaggtaagca cagcttgcaa attaaagcct              50

<210> SEQ ID NO 20
<211> LENGTH: 50
<212> TYPE: DNA
<213> ORGANISM: Artificial Sequence
<220> FEATURE:
<223> OTHER INFORMATION: amorce sens D2-Gibson AMG

<400> SEQUENCE: 20
tgcttacctc gtctactgca tgtatcctaa gcataaccgc tagagtactt              50
```